(12) United States Patent
Oon

(10) Patent No.: US 6,226,620 B1
(45) Date of Patent: May 1, 2001

(54) ITERATIVE PROBLEM SOLVING TECHNIQUE

(76) Inventor: Yeong Kuang Oon, 29 Darryl Street, Scoresby Vic 3179 (AU)

( * ) Notice: Subject to any disclaimer, the term of this patent is extended or adjusted under 35 U.S.C. 154(b) by 0 days.

(21) Appl. No.: 09/195,000

(22) PCT Filed: Jun. 11, 1997

(86) PCT No.: PCT/AU97/00362

§ 371 Date: Dec. 7, 1998

§ 102(e) Date: Dec. 7, 1998

(87) PCT Pub. No.: WO97/48059

PCT Pub. Date: Dec. 18, 1997

(30) Foreign Application Priority Data

Jun. 11, 1996 (AU) .................................................. PO5337
Sep. 12, 1996 (AU) .................................................. PO2319
Dec. 24, 1996 (AU) .................................................. PO4345

(51) Int. Cl.$^7$ .................................................. G06F 17/60
(52) U.S. Cl. .......................... 705/2; 705/1; 705/3; 705/7
(58) Field of Search .................................... 707/506, 352, 707/45, 4, 3, 1, 6, 5, 100; 706/46, 47; 379/93.24, 93.23, 93.21; 435/328, 320.1; 705/1, 2, 3, 7

(56) References Cited

U.S. PATENT DOCUMENTS

| | | | |
|---|---|---|---|
| 4,946,774 | * | 8/1990 | Oh .......................................... 435/7 |
| 5,027,318 | * | 6/1991 | Wischermann ........................ 365/78 |
| 5,276,612 | * | 1/1994 | Selker .............................. 364/413.06 |
| 5,277,188 | * | 1/1994 | Selker ................................... 128/696 |
| 5,324,077 | * | 6/1994 | Kessler et al. .......................... 283/54 |
| 5,367,619 | * | 11/1994 | Dipaolo et al. ....................... 395/149 |
| 5,418,948 | * | 5/1995 | Turtle .................................... 395/600 |
| 5,423,015 | * | 6/1995 | Chung ................................... 395/425 |
| 5,435,324 | * | 7/1995 | Brill ..................................... 128/897 |

(List continued on next page.)

FOREIGN PATENT DOCUMENTS

| | | |
|---|---|---|
| WO 94/00817 | 1/1994 | (WO) . |
| WO 95/00914 | 1/1995 | (WO) . |
| WO 95/12172 | 5/1995 | (WO) . |
| WO 95/35547 | 12/1995 | (WO) . |
| WO 96/13790 | 5/1996 | (WO) . |

OTHER PUBLICATIONS

Lowe, Henry J, Buchanan, Bruce G., Vriesm John K; Building a medical multimedia database system to integrate clinical . . . , Bull. Med. Libr, Assoc.;p57, Jan. 1995.*

Weber, David; Cyberhealth: A look back from 2019; Healcare Forum; v38; n1; p12–22, Jan.–Feb. 1995.*

Lempert, P.; Clinical Uses for Spreadsheets; PC Magazine, v4, n5, p283–285, Mar. 5, 1985.*

(List continued on next page.)

*Primary Examiner*—Vincent Millin
*Assistant Examiner*—Pedro Kanof
(74) *Attorney, Agent, or Firm*—Leydig, Voit & Mayer, Ltd.

(57) ABSTRACT

A method of implementing non-numerical spread sheets for the medical and legal domains using a computer-assisted iterative problem solving technique which starts from initial non-numerical data and develops possible solutions within a framework of an interrelation ship among pre-selected non-numerical data which are divided into a plurality of mutually exclusive categories differentiated according to readiness for decision making, including the steps of: displaying on a video display, a work sheet having a plurality of cells each corresponding to one of said mutually exclusive categories for displaying the non-numerical data; entering initial non-numerical data into respective cells in the work sheet; selecting a query designating at least a first cell in the work sheet with the initial non-numerical data as an input and requesting related non-numerical data for at least one cell of the plurality of cells in the work sheet; identifying non-numerical data for the at least one cell that is related to non-numerical data in the first cell; and inserting the identified non-numerical data into at least one cell in the work sheet as further information for consideration in developing possible solutions.

40 Claims, 26 Drawing Sheets

U.S. PATENT DOCUMENTS

| | | |
|---|---|---|
| 5,508,912 | 4/1996 | Schneiderman . |
| 5,511,553 * | 4/1996 | Segalowitz ............................ 128/696 |
| 5,693,623 * | 12/1997 | Della Valle et al. .................. 514/53 |
| 5,701,400 * | 12/1997 | Amado ................................... 395/76 |
| 5,704,044 * | 12/1997 | Tarter et al. ......................... 395/204 |
| 5,737,539 * | 4/1998 | Edelson et al. ...................... 395/203 |
| 5,766,886 * | 6/1998 | Studnicka et al. ............... 435/70.21 |
| 5,770,196 * | 6/1998 | Studnicka ........................... 424/133.1 |
| 5,813,002 * | 9/1998 | Agrawal et al. ......................... 707/5 |
| 5,821,123 * | 10/1998 | Studnicka ............................. 435/328 |
| 5,832,450 * | 11/1998 | Myers et al. ............................. 705/3 |
| 5,832,494 * | 11/1998 | Egger et al. ......................... 707/102 |
| 5,835,087 * | 11/1998 | Herz et al. ........................... 345/327 |
| 5,875,341 * | 2/1999 | Heckman et al. ....................... 705/7 |
| 5,883,124 * | 3/1999 | Samid ................................... 514/538 |
| 5,890,129 * | 3/1999 | Spurgeon ................................. 705/4 |
| 5,905,975 * | 5/1999 | Ausubel ................................. 705/37 |
| 5,918,208 * | 6/1999 | Javitt ...................................... 705/2 |
| 5,924,082 * | 7/1999 | Silverman et al. .................... 705/37 |
| 5,936,989 * | 8/1999 | Capasso et al. ....................... 372/45 |
| 5,956,707 * | 9/1999 | Chu ......................................... 707/3 |
| 5,997,871 * | 12/1999 | Gallo et al. ........................ 424/185.1 |
| 6,006,191 * | 12/1999 | DiRienzo ................................. 705/2 |
| 6,015,393 * | 1/2000 | Hovland et al. ..................... 600/587 |
| 6,030,838 * | 2/2000 | Telmissani ............................. 436/63 |

OTHER PUBLICATIONS

Grossman, Jerome H.; Plugged–In Medicine; Technology Review; p23, Jan. 1994.*

Rennels, Glenn D; Shortliffe, Edward H; Advanced Computing for Medicine; Scientific American; v257; p154(8), Oct. 1987.*

Taking the Tedium Out of Information Gathering; Infosystems; v31; n11; p120, Nov. 1984.*

Weed, L. "Medical Records Medical Education and Patient Care" *The Press of Case Western Reserve University*(1969).

Wong et al., "A Deductive Object–Oriented Database System for Situated inference in Law" *IEEE Transactions on Knowledge and Data Engineering*, vol. 8(3), pp. 496–503 (Jun. 1996).

* cited by examiner

FIG. 1

Encounter Form

File Edit Smalltalk Utilities

Name: Joe Blow       Worksheet 1       Date 21 Apr 1996

Presentation urineOutput^h

| P | L | U | M |
|---|---|---|---|
| url | | | Go | urine^bile
urine^blood
urine^colo-r
urine^fat
urine^flow
urine^gas
urine^glucose
urine^hair
urine^phosphate
urine@bedwetting
urine@frequency
urine@incontinence
urine@incontinence@impulse
urine@intermittancy
urine@pus
urine@tenesmus
urine@urgency
urineOutput^h
urineOutput^l
vagina@bleeding
vagina@discharge
vagina@irritation
vagina@pruritus
vagina@swelling
varicoseVeins@lowerLimb
varicoseVeins@thorax
vertigo
vesicles
vision^
vision^color

Links

Unity diabetesMellitus 0.2
hyper@paraThyroid 0.1

Management

| Add | < | > | CancPB | Cancel | WS > | WS < | WS Save | WS Load | ClrBk | BkSave | BkLoad |

The diabetes Mellitus Object-has data regarding Presentation, Links and Management

FIGURE 11. THE CLINICAL SPREADSHEET FLOWCHART

Name: FIGURE 16 | DATE | PRESENTATION | LINKS | UNITY | MANAGEMENT | Sheet Number:

ITERATIVE PROBLEM SOLVING TECHNIQUE

This invention relates to an iterative problem solving technique with particular application to both the medical and legal domains. Typically, this is computer assisted.

BACKGROUND TO INVENTION

Accountants started with work sheets which are ruled ledger forms, to get a picture of the financial status of a company. With computerisation, the manual work sheet has evolved into the electronic spreadsheet, a powerful tool indispensable to the accounting profession. In an electronic spreadsheet, there is a huge grid of cells in which one can enter numbers or formulae that will perform calculations based on the values of other cells. Other than the occasional spreadsheets that allow text string entries and provide basic string manipulations for use as headers, the spreadsheet is essentially a number calculation device. The spreadsheet calculates the numbers and gives the accountants quick answers to "What if?" type queries. The results of this "What if?" analysis are placed in the spreadsheet cells, this sets up the conditions for the next round of calculations with no manual transcription. The accountant's electronic spreadsheet is prodigious for tasks that require repetitive work with a hand held calculator. Hitherto, there is no such equivalent spreadsheet in the medical or legal domains with the capability of, during a client encounter, i) data entry and recording ii) performing "what if" calculations pertaining to client diagnosis and management, with results placed in cells for the next round of evaluation and iii) a spreadsheet with features such as scrollable work sheets that can be saved.

The present invention relates to an approach which allows the traditional accountant spreadsheet to be adapted to other applications, eg for use in a real or simulated patient or client encounter environment or in the legal environment. Whilst the following description is with reference to the medical and legal fields, the invention is not so limited.

Traditionally the manual/electronic medical record keeping may be divided effectively in three modes: 1) fully manual, 2) manual cum electronic, and 3) filly electronic medical record system.

Current manual medical record systems are not properly designed from the information flow viewpoint. In particular, hitherto there is difficulty in presenting encounter data and global patient data using the same medical model. The end result is poorer patient care which can be attributed to medical information being hidden or lost in the jungle of data in a patient medical record regardless of its medium. While the best of the current crop of medical record systems as epitomised by the Problem Oriented Medical Record/ Subjective Objective Assessment Plan model (POMR/SOAP) by Lawrence Weed (Medical Records, Medical Education and Patient Care. Cleveland: Case Reserve Press 1969.), attempts to structure medical record in a logical manner, it still does not lend itself to smooth information flow and effective computerisation as there is a schism in the day of consultation encounter data model and the patient global health status data model.

The present day medical record systems, regardless of whether they are manual or electronic, do not promote clear thinking in the mind of the clinician, pointedly there are no formal relationships among the various sections of the medical record. Present day record systems can be described as incongruous, non-optimised, and when computerised end up as a non-optimal systems also.

Current manual medical records are not designed for quick and accurate evaluation of patient clinical health status. Patient health data is often buried in clinical notes, important and exceptional patient data are often hidden from the health workers due to poor record design. This leads to medical accidents and potential litigation. There is potential to achieve better health outcomes and better quality patient care by not doubling on medical investigations, not missing tests that ought to be done, maximising available information and reducing litigation by overcoming current weaknesses in medical recording. Such weaknesses include the lack of a section for well defined diagnoses to precede treatment and sections reserved for evidence to support such clear diagnostic entities.

There also exists the promise of improved patient care by the computerisation of patient medical record. However this is tempered by the uncertainty over the veracity and legality of computerised medical records in medical litigation. This is one argument to keep some form of written notes. Keying in notes or dictating into a microphone by the clinician during the consultation process is acceptable only to a minority of doctors who are also technologically competent. The above would suggest that an ideal health record system for some doctors would comprise both manual and electronic elements.

Current medical record design is not conducive to rapid and effective evaluation of patient clinical status in its paper format. Any hope of leveraging the power of electronic computation into the medical record domain is predicated on a congruent patient health data model that is functional in both the manual and electronic medical record situations. Hitherto the paper medical record has been hard to computerise as there does not exist a congruous data model of the patient medical record that is effective for both the manual and the electronic medical record version. The Problem Oriented Medical Record of Weed is difficult to computerise as there is a separate data model for the encounter called SOAP and a global model of the patient called the problem list.

Another barrier to medical computerisation and mentioned above, and of a greater magnitude, is that pertaining to disruption of the doctor's work flow during the consultation. The traditional approach of pen and paper works well during a consultation as there is minimal disruption to the consultation process. During this process, the doctor has to concentrate on verbal and body language cues to achieve optimal communication with the patient; while at the same time, in a discrete manner makes notes and conducts an evaluation process in his or her professional mind.

To type in notes or to dictate into a voice recognition system during a consultation are strong disincentives for the majority of doctors to computerise their medical notes. Yet the computer is a powerful tool for making quick evaluation of patient status such as calculating, tracking the date of the last pap smear and recalling the patient. For instance in the tracking of pap smears the computer can easily work out to the nearest day since the last pap smear in a mere instant. The computer is also excellent in detecting drug interactions and disease-drug interactions. Hence, the quality of medical care can be promoted in a fully computerise medical record, as long as the medical data captured is structured in a way to be evaluated by the computer program. The scanning of word processed documents and medical images such as X-ray pictures to be placed into the patient electronic folder does not make use of the computer evaluation capacity at all and hence is a second rate implementation of the electronic medical record.

An inimical influence to the proper design of the manual medical record is the traditional teaching in medical schools to countless generations of medical students of the need to separate clinical symptoms and signs when approaching a patient clinical problem. In this paradigm, the consultation process begins with history taking (the collection of symptoms), this is followed by the physical examination of the patient (the collection of signs). Hence traditional medical notes will have two separate categories, one for symptoms and the other for signs. The traditional model of medical notes go like this: symptoms→physical examination/physical signs→assessment→treatment plan This current art of the manual medical record system is described in the POMR/SOAP model by Dr L Weed (Medical Records, Medical Education and Patient Care. Cleveland: Case Reserve Press 1969.). POMR stands for Problem Oriented Medical Record while SOAP stands for Subjective Objective Assessment Plan.

This structured POMR/SOAP model is a vast improvement over other unstructured methods. Unstructured medical record keeping may lead to poor quality patient care and the propensity for medical negligence increases. Weed's ideas are implemented in the Royal Australian College of General Practitioners current paper medical record system and widely used in teaching hospitals in many countries.

In the problem oriented model, any unresolved or significant medical problem, be it a symptom, a sign, a diagnosis or an abnormal pathology result is collected into a numbered list. This problem list is placed on the first few pages of the patient record to jog the doctors mind as to the problems he or she has to grapple with. In the POMR/SOAP model, the ongoing case notes arising from consultation are encapsulated into the following categories referred to as SOAP: 1) Subjective—symptoms 2) Objective—physical examination/signs and objective test results 3) Assessment—doctor's opinion, but not necessarily a diagnosis 4) Plan—treatment, investigations.

However, the following are weaknesses of current medical record design, in particular POMR/SOAP.

1) The SOAP model is designed only for recording the encounter. The SOAP model cannot be used to represent patient global health status. For a comprehensive patient evaluation, we need in addition to clinical data collected for the encounter, at least the following information: current and past diagnoses, current medications, diagnostic imaging results, diagnostic non-imaging results. The POMR/SOAP model provides a problem list for the purpose of a comprehensive evaluation. An ideal health data model should be the same one used to represent encounter as the one used for global patient health status.

2) With the SOAP model, there is a self imposed chasm between symptoms and signs when recording. In reality, there is no clear logical demarcation between symptoms (subjective) and signs(objective) from an information science viewpoint. The patient can present to the doctor and clearly describe his i) lump ii) rash or iii) jaundice. These three entities are really physical examination signs or objective (in the SOAP terminology) findings. Often the patient volunteers the right diagnosis as well. Using these examples, all these data should strictly be recorded under as "symptoms" as they are information provided by the patient.

While the practice of eliciting symptoms and then proceeding to do a detailed physical examination cannot be faulted, there is no logical reason for the clinical recording to reflect actual clinical practice except for the purpose of training medical students.

3) With SOAP, abnormal test results are lumped in with signs. With the march of medical technology, the old paradigm is being left behind. Laboratory and radiology results play an overwhelming role in patient diagnosis, yet scores no space in the traditional paradigm or get lumped with clinical signs. A chest x-ray beats the most astute clinician with his stethoscope. From the information science viewpoint, the quality of a physical finding by examination is generally "less sure" compared to say a radiological finding or say an abnormal chemical pathology test. Abnormal laboratory and radiological test results are of a different predictive value and hence demands an almost exclusive category separate from clinical signs.

4) The assessment section of the traditional encounter model often holds the opinion of the clinician at the end of the consultation. It may be vague or non-diagnostic labels, such as "?appendicitis" "fever for investigation" "chronic abdomen pains". Often at the end of a patient encounter, a diagnosis is not even possible or at best only a provisional diagnosis made. From the information science viewpoint, the quality of the data placed in the Assessment section of SOAP notes are hard to evaluate in relationship to treatment.

5) There is a paradigm shift in the practice of medicine towards a heavy reliance on technology. Increasingly we see patients who are completely asymptomatic walk into a clinic and subject himself to screening tests for metabolic abnormalities, infectious disease or cancer. Not withstanding the fact that the art of eliciting clinical signs is important in medicine, it is clear that the results of a computerised axial tomography scan are of a different level of quality as compared to physical examination by palpation. Traditional clinical encounter recording has not integrated the modern practice of medicine with its current emphasis on technology.

6) The traditional medical record does not provide a tight framework for human/computer evaluation of the patient. For the purpose of machine evaluation one can refer to the computer chess paradigm. The evaluation of a chess position in a computer chess program may be used as the metaphor for the evaluation of a patient health status. In a chess position, the machine evaluates a position numerically based on a belief system comprising the following elements a) material advantage b) tempi-rapid development c) space advantage d) initiative—ability to launch threat e) attack on enemy pieces f) King safety g) piece activity, mobility and coordination h) pawn structure. With reference to each of these categories, the chess program ranks each candidate move with a numeric rating based on the strength of the resultant chess positions. A viable medical record data model is to be constructed like a belief system where the elements are linked in more formal relationships than we have seen in the current breed of medical records.

7) Overall, the existing encounter models lack precision in their theoretical foundation for the building of a manual/electronic medical record that provides a running score sheet of the patient health status from the encounter to the global level. POMR/SOAP is not facilitated for patient evaluation in the sense that the problem list structure is not closely relate to the SOAP encounter structure.

In summary, the traditional medical record model is not optimally designed from the information processing viewpoint. This poor manual record design means that they are not designed for easy computerisation.

Hence the problem is to come up with a) an appropriate evaluation model of the medical record that is effective and congruent for both the manual, hybrid manual/electronic, and fully electronic format of the medical record; b) a data model applicable for use in both the encounter and the global health data recording and evaluation; and c) overcome the man-machine interface problem (meaning no typing, no speaking into microphone when talking to patient) in computerisation of the medical record.

Turning now to the legal environment, during a meeting with his client, the lawyer needs to record the case details and constantly make evaluations of legal problems, resulting in dispensation of sound legal advice based on statute laws or precedents in common law cases. The traditional paradigm is based on textual narration of legal cases and key word search of electronic databases. Traditional legal practice has been quick to latch on to technology with computerised search engines and on-line databases.

The traditional legal model lacks the precision, required by computers, in its theoretical foundation for the building of an electronic legal spreadsheet. At issue is the creation of a legal belief system suitable for computerisation.

DESCRIPTION OF THE INVENTION

Accordingly there is provided a method of implementing a computer-assisted iterative problem solving technique which starts from initial non-numerical data and develops possible solutions within a framework of an interrelationship among pre-selected non-numerical data which are divided into a plurality of mutually exclusive categories, including the steps of:

displaying on a video display, a work sheet having a plurality of cells each corresponding to one of said mutually exclusive categories for displaying the non-numerical data;

entering initial non-numerical data into respective cells in the work sheet;

selecting a query designating at least a first cell in the work sheet with the initial non-numerical data as an input and requesting related non-numerical data for at least one cell of the plurality of cells in the work sheet;

identifying non-numerical data for the at least one cell that are related to non-numerical data in the first cell; and inserting the identified non-numerical data into the at least one cell in the work sheet as further information for consideration in developing possible solutions.

Preferably, the step of entering includes displaying a pick list of non-numerical data on the video display, selecting an entry of the pick list, and displaying the selected entry in a respective cell in the work sheet.

Alternatively, the step of entering may be achieved by receiving through an input device, an alphanumeric input indicating a non-numerical datum. Typically this may further include parsing the received alphanumeric input to determine the indicated non-numerical datum.

Preferably, the method further includes providing a plurality of program objects each corresponding to one of the pre-selected non-numerical data, and wherein the step of identifying includes transmitting a request for related data according to the query to program objects corresponding to the non-numerical data in the first cell.

Preferably, the method further including saving contents of the cells in the work sheet before the query as one spreadsheet page.

Typically, the mutually exclusive categories include categories (preferably four) differentiated according to readiness for decision making.

Preferably, the step of identifying includes obtaining non-numerical data for a further cell in the work sheet that are related to the non-numerical data in the first cell, and obtaining non-numerical data for the at least one cell that are related to the obtained non-numerical data for the further cell.

Preferably the method further includes displaying a probability of occurrence associated with at least one of the identified related data in the at least one cell.

As mentioned above the invention has particular application to the medical field. In this respect, a method of implementing a computer-assisted iterative clinical problem solving technique is provided which starts from initial clinical data and develops possible solutions within a framework of an interrelationship among pre-selected clinical data which is divided into a plurality of mutually exclusive categories, including the steps of:

displaying on a video display a work sheet having a plurality of cells each corresponding to one of said mutually exclusive categories for displaying the clinical data;

entering initial clinical data into respective cells in the work sheet;

selecting a query designating at least a first cell in the work sheet with the initial clinical data as an input and requesting related clinical data for at least one cell of the plurality of cells in the work sheet;

identifying clinical data for the at least one cell that are related to clinical data in the first cell according to the query; and inserting the identified clinical data into the at least one cell in the work sheet as further information for consideration in developing possible solutions.

Preferably, the step of entering includes displaying a pick list of clinical data on the video display, selecting an entry of the pick list, and displaying the selected entry in a respective cell in the work sheet.

Preferably the method further includes providing a plurality of program objects each corresponding to one of the pre-selected clinical data, and wherein the step of identifying includes transmitting a request for related clinical data to program objects corresponding to the clinical data in the first cell.

Preferably the method further includes saving contents of the cells in the work sheet before the query as one spreadsheet page.

Typically, the mutually exclusive categories include categories differentiated according to readiness for diagnosis. For example, the mutually exclusive categories may include a first category which includes symptoms and signs, a second category which includes clinical test results, and a third category which includes diagnoses. These categories may also include a fourth category which includes prescribed treatment and investigations.

Preferably, the step of identifying includes obtaining clinical data for a further cell in the work sheet that are related to the clinical data in the first cell, and obtaining clinical data for the at least one cell that related to the obtained clinical data for the further cell.

Preferably, the method further includes displaying a probability of occurrence associated with at least one of the identified related clinical data in the at least one cell.

As mentioned above the invention has particular application to the legal area. In this respect, a method of implementing a computer-assisted iterative legal problem solving technique which starts from initial legal data and develops possible solutions within a framework of an interrelationship among pre-selected legal data which is divided into a plurality of mutually exclusive categories, including the steps of:

displaying on a video display a work sheet having a plurality of cells each corresponding to one of said mutually exclusive categories for displaying the legal data;

entering initial legal data into respective cells in the work sheet;

selecting a query designating at least a first cell in the work sheet with the initial legal data as an input and requesting legal data for at least one cell of the plurality of cells in the work sheet that are related to legal data in the first cell;

identifying legal data for the at least one cell that are related to the legal data in the first cell according to the query; and inserting the identified legal data into the at least one cell in the work sheet as further information for consideration in developing possible solutions.

Preferably, the step of entering includes displaying a pick list of legal data on the video display, selecting an entry of the pick list, and displaying the selected entry in a respective cell in the work sheet.

Preferably, the method further includes providing a plurality of program objects each corresponding to one of the pre-selected legal data, and wherein the step of identifying includes transmitting a request for related legal data according to the query to program objects corresponding to the legal data in the first cell.

Preferably, the method further includes assigning a key term for each of the pre-selected legal data for identifying the program object corresponding to said each pre-selected legal datum and for representing said each pre-selected legal datum in a respective cell in the work sheet.

Preferably, the method further includes saving contents of the cells of the work sheet before the query as one spreadsheet page.

Typically, the mutually exclusive categories include categories differentiated according to readiness for adjudication. For example the mutually exclusive categories may include a first category which includes dispute-related facts, a second category which includes legal precedents, and a third category which includes legal principles. These categories may further include a fourth category which includes legal remedies.

Preferably, the step of identifying includes obtaining legal data for a further cell in the work sheet that are related to the legal data in the first cell, and obtaining legal data for the at least one cell that are related to the obtained legal data for the further cell.

In yet another embodiment of the invention separate to the above, a method is provided of recording patient specific clinical data for evaluation of patient status, where clinical data has been divided into a plurality of mutually exclusive categories including the steps of:

providing an encounter form which has a plurality of cells each corresponding to one of said mutually exclusive categories; and entering the patient specific clinical data collected during at least one patient encounter into respective cells in the encounter form according to the respective categories to which the collected clinical data belong.

Preferably, the method further including the steps of:

providing a global status form which has a plurality of cells each corresponding to one of said mutually exclusive categories; and posting the collected clinical data in the at least one encounter form into respective cells in the global status form.

Preferably, the step of posting includes electronically scanning the cells of the encounter form to identify the collected clinical data and the respective categories of the collected clinical data, and storing the collected clinical data into respective cells of the global status form.

Preferably, the method further includes the steps of providing a global inactive status form which has cells corresponding respectively to the mutually exclusive categories, and transferring clinical data posted in the global status form that have become inactive into respective cells in the global inactive status form.

Preferably, the step of entering includes recording in the encounter form a date of generation for each datum of the collected clinical data.

Preferably, the mutually exclusive categories consist of four categories. Typically the categories are differentiated according to readiness for diagnosis. For example, a first category which includes signs and symptoms, a second category which includes clinical test results, and a third category which includes diagnoses. These categories may also include a fourth category which includes treatment and investigations.

In yet another embodiment of the invention, there is provided, a recording system for recording clinical data for evaluation of patient status including:

a reference listing having a plurality of mutually exclusive categories;

an encounter form having a plurality of cells each corresponding to one of said mutually exclusive categories to receive;

wherein clinical data collected during at least one patient encounter is entered into respective cells in the encounter form according to the respective categories to which the collected clinical data belong.

Accordingly in the various embodiments the invention can provide on the one hand, the clinician with a spreadsheet tool for use in patient care to effect efficient diagnosis, management and data recording. On the other hand the equivalent legal spreadsheet likewise, will provide the lawyer the same benefits with regards to solving and recording of legal problems. It will provide the same utility to them comparable to the analogy of the accountant and his spreadsheet. The data model and methods for both the medical and legal spreadsheets are cognate.

DETAILED DESCRIPTION OF PREFERRED EMBODIMENTS OF THE INVENTION

For ease of perusal, there is a separation of the following descriptions for the medical and legal spreadsheets where possible. Below, there are complete separate detailed descriptions of the respective preferred spreadsheets even though they share the same logical framework and methods. A glossary is provided at the end of the specifications. There is also a paper equivalent to the medical spreadsheet which forms the basis of an effective manual/hybrid medical record system. The detailed descriptions of the preferred embodiments are split into these two topics 1) the medical or clinical spreadsheet and the paper/hybrid medical record modelled on the medical spreadsheet; and 2) the legal spreadsheet.

The Medical or Clinical Spreadsheet

This tool provides a means for recording clinical data and means for extensive What-If? type processing. The input and output of the medical spreadsheet process are based on the cells of the spreadsheet during a real or virtual patient encounter. As the input and output arising from the patient evaluation are all cell based, this provides the powerful paradigm of iterative and hypothetical type problem solving. Applying the same spreadsheet metaphor, the pages (or work sheets) of this medical spreadsheet can be scrolled back and forth and get saved for future reference. These and other objects of the present invention of the medical spreadsheet are achieved by overcoming the aforementioned technical barriers with the use of a new computer model to represent the patient health status at any point in time.

This model provides a suitable clinical data model for use in a medical spreadsheet; supports a logical framework for the recording of the clinical encounter and display of cumulative patient data. The model is called the Graduated Discrete Definition Model or GDDM for short. It provides the means to model the clinical state of a patient by the use of clinical descriptors based on the GDDM. With the Graduated Discrete Definition Model, the classification of all clinical data is according to one criterion—with reference to its degree of definition in terms of readiness for medical treatment and/or prognostication. With such a classification framework, at one end of the scale there would be the not-yet-defined clinical data such as a clinical symptom or sign, these clinical data items do not have the degree of definition necessary for treatment or prognostication. At the other end of the spectrum, we have the well-defined clinical data such as a diagnosis which has a clear prognosis and treatment. There can be one or more intermediate categories positioned between the not-yet-defined and the well-defined categories.

One preferred option of this present invention has only one intermediate category called the about-to-be-defined category. To complete this classification model, there is an additional category to include all extrinsic patient clinical data comprising treatment and investigations. Alternately, a separate category each for treatment and investigations is an option.

One preferred option of this present invention is to use a single management category comprising both treatment and investigations to complete the model.

Hence one preferred option of this present invention is a tetrad version of the Graduated Discrete Definition Model. This name describes the distinct individual, mutually exclusive, marked intervals based on degree of definition. The tetrad version of the Graduated Discrete Definition Model is called PLUM which stands for Presentation, Links, Unity and Management.

All clinical data to describe the patient status and patient management are classified into the four categories of: 1) Presentation—this comprises all Not Yet Defined clinical data such as symptoms and signs. 2) Links—this comprises all About To Be Defined clinical data such as the abnormal test results and provisional diagnoses made by doctor, these entities are not specific enough for treatment and/or prognostication but better defined as compared with the Not Yet Defined data. 3) Unity—this comprises all Well Defined clinical data of the clear diagnosis type where there is specific treatment and/or prognostication. 4) Management— this comprises laboratory and radiological investigations, drug treatment, procedures and process of care. PLUM represents the four categories of the tetrad version of the Graduated Discrete Definition Model.

The clinical encounter form has four cells, each representing the four categories of PLUM. The Presentation cell is reserved for Not Yet Defined clinical data. The Links cell is reserved for About To Be Defined clinical data. The Unity cell is reserved for Well Defined clinical data. The Management cell is for clinical data related to treatment and investigations. The PLUM model provides the logical framework for the spreadsheet. The Graduated Discrete Definition Model of which PLUM is the tetrad implementation, is congruent with the underlying logic of the doctoring process which is the processing of unclear clinical information to resolution in the form of a well defined diagnosis. This is followed up with treatment, or investigation if resolution is not possible.

The Graduated Discrete Definition Model ameliorates the drawbacks of the traditional paradigm and classifies all clinical data into mutually exclusive categories.

The design of the medical spreadsheet obviates the need for the clinician to type as there is a comprehensive pick list with search facility. The cells of the spreadsheet are all text panes that the user can edit. The layout of each page of the medical spreadsheet is a collection of four cells, respectively named P, L, U, and M and incorporates a pick list. These four cells can be arranged as a 4×1 or a 2×2 arrangement according to user preferences. With a pick list on the right of the screen (see FIG. 1), the clinical data item selected will automatically be positioned correctly in one of the four cells. The selected item itself is a key to a medical entity (represented by a computer software object) which keeps track of its own membership of one of the PLUM categories.

The What-If query is launched from the drop down menu, of which there is a choice of over 50 useful types out of a possible 225. After each computer assisted evaluation, the work sheet is updated and the work sheet page number is incremented by one. The PLUM work sheet on the screen is called a page, it depicts a real or hypothetical image of the patient status and can be saved and recalled. A work sheet depicting only the known true events regarding the patient can be saved as the factual encounter record for that consultation. A collection of work sheet pages can be saved as a book, for future re-loading and use.

The medical spreadsheet performs evaluations and answers "what if" and "what should I do next?" queries by the simple expedient of selecting an item from a drop down menu rather than via complicated textual queries of the SQL ( Structured Query Language ) type. During an evaluation, the contents of the cells provide the input for the evaluation unit. The output is stored back in the appropriate cell. Based on the four cells, there are 225 possible types of queries, see detailed description.

The following types of queries (with explanation in traditional medical vernacular in parenthesis) are the more useful ones:

a) Given Presentation and Links, show Unity
   (Given symptoms and signs and the abnormal laboratory or radiological tests, show differential diagnosis)
b) Given Unity, show Management
   (Given diagnoses, show treatment)
c) Given Unity, show Presentation and Links
   (Given diagnoses, show symptoms and signs and abnormal tests)
d) Given Management, show Presentation
   (Given treatment, show adverse symptoms and signs)
e) Given Unity and Management, show Unity
   (Given diagnosis and treatment, show more diagnoses arising from disease—drug interactions)
f) Given Unity, show Unity
   (Given a list of diagnoses, infer a further diagnosis that might unite several diagnoses)

g) Given Links, show Unity
   (Given a abnormal laboratory or radiological result, what are the diagnoses)
h) Given Presentation, Links and Unity, show Unity
   (Given a list of diagnoses, prune those diagnoses that do not have the listed symptoms, signs and laboratory results).

All clinical entities such as drugs, symptoms, signs, diagnosis, radiology, pathology results are treated as equal objects, each object knows if it is a Presentation (Not-Yet-Defined), or a Links (About-To-Be-Defined), or a Unity (Well-defined) or a Management object. All these medical objects are classified in a hierarchy similar to the biological Linnean system (see later) with the four phylla of Presentation, Links, Unity and Management. A Well-Defined Object knows all the Not-Yet-Defined, About-To-Be-Defined and Management objects associated with it, and their probabilities. The output of the evaluations are into the cells, and are ranked on the basis of probability, this probability rating is quoted just after the medical entity. The medical spreadsheet enables critical computer evaluation of the patient status at every stage of the consultation as pre-existing medical data can be imported from the medical record. The medical spreadsheet is designed to be used in an iterative manner for solving clinical problems. As a result of each query, the cells are updated, the user can choose to edit the cells and a further query can be launched. Each cell is a text pane, for the evaluation exercise only the first word of each new line is parsed. This design allows the doctor to enter free text to augment his notes. Practical output of the spreadsheet includes 1) prescription writing 2)ordering of pathology and radiology tests as the contents of the management cell are readily diverted to the prescription or pathology request modules.

In one preferred form of the invention, the medical spreadsheet functions as fully integrated with the electronic medical record. Importation of clinical data regarding the existing set of clinical problems, medications, results of investigations of the existing electronic medical record into the medical spreadsheet is achieved by a click of a button.

In another preferred form of the invention, the Management category of the clinical data model is further classified separately into treatment and investigation. This leads to a screen with an additional cell. More graduated levels of definition of the clinical data beyond the four levels have been tried, but that increases complexity to the user. Intrinsic clinical data can be further classified beyond the levels of 1) not-yet defined 2) about-to-be-defined and 3) well-defined. This leads to a screen with additional cells due to the increased number of categories. The preferred option is to keep the application simple for the user. Hence the four cells of Presentation, Links, Unity and Management (comprising both treatment and investigations), appear to be an efficient solution.

In another preferred form of the invention, the medical spreadsheet functions as a stand alone program. In the stand alone mode the medical spreadsheet is a library resource, a clinical tutor and is able to sharpen the skills of the clinical student using the spreadsheet in a discovery mode.

Also an improved system of medical record keeping is achieved using the same tetrad PLUM model. It spans across the manual/electronic medical record divide and functions effectively in three modes: 1) fully manual: 2) manual cum electronic; and 3) fully electronic medical record system. In this medical record system, the patient health data inside the clinical encounter is recorded in the tetrad format while other instances of the same tetrad holds the global active, global inactive and global log components of the health record, these components represent the overall health status of the patient.

The Plum Layout of the Medical Spreadsheet

As mentioned above, the acronym PLUM stands for presentation, links, unity and management.

The layout of the medical spreadsheet is based on the PLUM tetrad of the Graduated Discrete Definition Model. There are four cells lined up in one column in one implementation or alternatively, as a two by two arrangement. The four cells are named P, L, U, and M; starting from the top. These four cells are directly mapped to the four categories of the tetrad version. The P or Presentation cell holds only the NYD events. The L or Links cell hold only ATBD events. The U or Unity cell contains only WD events while the M or Management cell holds events of the extrinsic category exclusively.

On the right of the screen is a pick list of all clinical event descriptors. A selection made on this list will result in the spreadsheet looking up the category that the selected item belongs to. It will then be updated in a new line in the correct PLUM cell. The user can manually type input into the cell, however the pick list will lead to fewer parsing errors when the calculation is launched.

There is the option of importation of global or cumulative patient data into the encounter spreadsheet from the Global Active PLUM (see later) and the Global Inactive PLUM.

Method of Operation

The implementation of the spreadsheet is based on the concept of objects and objects responding to messages. All the events in the tetrad model are objects and respond to messages. For example the Unity object of Diabetes Mellitus when sent a query message of list_Presentation will provide a list of symptoms and signs with the associative probabilities ranging from 0 to 1. The message of list_Links will list all the pathology and radiological results associated with DiabetesMellitus with the associative probabilities ranging from 0 to 1. While the message list_Management will list all the common treatment for diabetesMellitus.

Method of operation for queries of the type:

P→U

This query reads as "Given Presentation show Unity". The doctor or medical student selects cough by scrolling through the pick list or narrow the pick list by typing "cou" in the search pane next to the GO button. He then proceeds to pick "cough". The same procedure is followed to pick "hemoptysis". Both terms will be automatically inserted into the P cell. A query for differential diagnosis of say the symptoms of cough and hemoptysis will lead to
bronchitis@acute [0.3]
carcinoma.bronchus [0.2]
tuberculosis [0.1]
being outputted in the Unity cell. The figures in the square parentheses denote the probability rating of the diagnosis. The User can also chose not to display the parentheses. The output to the Unity cell is ranked according to the probabilities. On launching the P→U query, the program will search for all Unity objects with Presentation events conforming to cough and hemoptysis.

L→U

This query reads as "Given Links show Unity".

If the user picks a Links object such as xr.chest*spot—this means an x ray of the chest that is abnormal being described as a spot. On the launch of the query, the program will interrogate the Links object labelled as xr.chest*spot for its list of associated Unity (diagnoses) objects and associated probabilities. The output in the Unity cell will be:
carcinoma.bronchus [0.2]
tuberculosis [0.1]

M→P

This query reads as "Given Management show Presentation".

If the user picks penicillin , on launching the query, the program will interrogate the Management object called penicillin for its list of adverse reactions. The output will be in the presentation cell.
stomach@pain [0.02]
stomach@nausea [0.01]
vomiting [0.01]
diarrhea [0.01]

M→U

"Given management show unity". Given a single treatment, show diagnoses, that is a therapeutic index. However if there is more than one treatment, it will show adverse drug to drug interactions leading to diagnoses listed in unity cell. Using the example of penicillin, on launching the query, the program will interrogate the penicillin object for its list of Unity objects where penicillin therapy is appropriate. The output in the Unity cell will show
tonsillitis
infection<streptococcusPyogenes
infection<neisseria

U→P

This query reads as "Given Unity show Presentation". Say the user picks tonsillitis into the Unity cell. On launching the query, the program will interrogate the Unity object for its list of Presentation with associated probabilities. The output will be in the Presentation cell of
throat@pain [0.7]
fever [0.6]
muscle@pain [0.2]
breath@bad [0.2]

U→L

This query reads as "Given Unity show Links". Say the user picks tonsillitis into the Unity cell. On launching the query, the program will interrogate the Unity object for its list of Links with associated probabilities. The output will be in the Presentation cell of
microAndCulture.throat* [0.5]
whiteCellCount*h [0.3]

U→M

This query reads as "Given Unity show Management". Say the user picks tonsillitis into the Unity cell. On launching the query, the program will interrogate the Unity object for its list of Management. The output will be in the Presentation cell of
penicillin
erythromycin
amoxycillin
cephalexin

P→LU

This query reads as "Given Presentation show Links and Unity". Say the user picks hemoptysis into the Presentation cell. On launching the query, the program will interrogate the Presentation object for its list of Unity objects with associated probabilities. From the collection of Unity objects, interrogate these objects for their lists of Links. The output will be in the Unity cell will be
bronchitis [0.5]
carcinoma.bronchus [0.2]
tuberculosis [0.1]
The output in the Links cell will look something like (comments in parentheses)
xr.chest*spot (x ray of chest abnormal with a spot)
micro@sputum* (micro and culture of sputum abnormal)
test@(mantoux* (abnormal mantoux test)

P→UM

This query reads as "Given Presentation show Unity and Management". Say the user picks hemoptysis into the Presentation cell. On launching the query, the program will interrogate the Presentation object for its list of Unity objects with associated probabilities. From the collection of Unity objects, interrogate these objects for their lists of Management. Effectively two queries in sequence of 1) P→U 2) U→M.

L→PU

This query reads as "Given Links show Presentation and Unity". This query is actually the following queries done in sequence 1) L→U 2) U→P.

L→UM

This query reads as "Given Links show Unity and Management". This query is actually the following queries done in sequence 1) L→U 2) U→M.

M→LU

This query reads as "Given Management show Links and Unity". This query is actually the following queries done in sequence 1) M→U 2) U→L.

M→PU

This query reads as "Given Management show Presentation and Unity". This query is actually the following queries done in sequence 1) M→U 2) U→P.

U→PL

This query reads as "Given Unity show Presentation and links". This query is actually the following queries done in sequence 1) U→P 2) U→L.

P→LUM

This query reads as "Given Presentation show Links Unity and Management". This query is actually the following queries done in sequence 1) P→U 2) U→L and 3) U→M.

L→PUM

This query reads as "Given Links, show Presentation, Unity and Management". This query is actually the following queries done in sequence 1) L→U 2) U→P 3) U→M.

U→PLM

This query reads as "Given Unity show Presentation, Links and Management". This query is actually the following queries done in sequence 1) U→P 2) U→L 3) U→M.

PL→U

This query reads as "Given Presentation and Links, show Unity". This query is actually the following queries done in sequence 1) P→U 2) L→U.

This is followed up by the collation and ranking of the U contents.

PU→L

This query reads as "Given Presentation and Unity, show Links". This query is actually the following queries done in sequence 1) P→U 2) U→L.

This is followed up by the collation and ranking of the L contents.

PU→M

This query reads as "Given Presentation and Unity, show Management". This query is actually the following queries done in sequence 1) P→U 2) U→M.

This is followed up by the collation and ranking of the M contents.

PL→UM

This query reads as "Given Presentation and Links, show Unity and Management". This query is actually the following queries done in sequence 1) P→U 2) L→U 3) U→M.

PLU→U

This query reads as "Given Presentation, Links and Unity, show Unity". This query is actually the following queries done in sequence 1) P→U 2) L→U. The intersection of the sum of these two outputs and the original U contents gives the list of Unity objects consistent with Presentation and links. This query is useful to trim long lists of differential diagnoses.

P→P

This query reads as "Given Presentation show Presentation". This query is to query the Presentation objects to release more associated Presentation objects. The implementation details are: 1) P→U 2) U→P. Like a presentation object such as cough will cause the output of cough
hemoptysis
wheezing
shortnessOfBreath

L→L

This query reads as "Given Links show Links". This query is to query the Links objects to release more associated Links objects. The implementation details are: 1) L→U 2) U→L.

This query is useful for suggesting more appropriate tests.

U→U(max)

This query reads as "Given Unity show Unity maximised".

In the case of one Unity object, it queries the Unity object to release more associated Unity objects. One implementation is of the form: 1) U→L 2) L→U and 1) U→P 2) P→U. These sequences produce a longer list of diagnostic possibilities.

U→U(min)

This query reads as "Given Unity show Unity minimised".

In this case of multiple Unity objects, the query tries to shorten the list by unifying several diagnoses into one diagnosis. For example if the Unity cell has the following:
fracture
calculus.kidney
hypertension
it will evaluate to hyperparathyroidism

M→M

This query reads as "Given Management show Management". This query is to query the management objects to release more associated management objects. This is a useful query for alternate therapy, for instance in cases of drug allergy. The implementation details are: 1) M→U2) U→M.

UM→U

This query reads as "Given Unity and Management show Unity". This query is to query the interaction of management objects with Unity objects to show diagnostic possibilities arising from disease drug interactions.

The pathology/radiology request output module is activated from a drop down menu. The contents of the Management pane is put into a collection. The elements of this collection are put into a do loop which selects only laboratory/radiology objects. The results are placed in dialogue box, items selected are printed onto a request form, utilising information held in the medical record, the medical record is then updated.

The drug prescription printing module is activated from a drop down menu. The contents of the Management pane is put into a collection. The elements of this collection are put into a do loop which selects only drug objects. The results are placed in a dialogue box, items selected are printed onto a prescription form, utilising information held in the medical record, the medical record is then updated.

The patient education module is activated from a drop down menu. The contents of the Management pane is put into a collection. The results are placed in a dialogue box and educational information related to items selected are printed out as patient education leaflets.

The PLUM Query Language

As mentioned above, in the preferred tetrad implementation of the Graduated Discrete Definition Model, there are four cells, P, L, U and M cells. All the possible permutations of queries can be calculated using the nCr formula of $$nCr:=n!/r!(n-r)!$$

This standard permutation formula describes the number of selections of n different objects taken r at a time. That is the number of r subsets that can be formed from an n set. As the number of cells that can be recruited for input ranges from 1 to 4, the total number of permutations are:

$$4C1+4C2+4C3+4C4=4+6+4+1=15$$

Hence the number of permutations for input from the four cells is fifteen.

Likewise the number of permutations for output is also fifteen.

Hence the theoretical maximum of query types based on all permutations of input and output into four cells is 15×15=225. The medical query language comprises these 225 permutations of drawing input from the four cells and channelling output into permutations of these four cells.

However the majority of queries are of no practical value, such as: "Given links and management, show presentation, links, unity and management." or "Given presentation, unity and management, show links". Most of the useful queries have output of the evaluation directed into other cells rather than the input cells. However there are instances of useful queries whereby the output can be channelled back into the input cell, see examples later.

The more practical queries can be classified according to the following types where the output is directed away from the input cell(s):

1) 1 cell input and output in 1 cell.
2) 1 cell input and output in 2 cells.
3) 1 cell input and output in 3 cells.
4) 2 cell input and output in 1 cell.
5) 2 cell input and output in 2 cells.
6) 3 cell input and output in 1 cell.

Queries of the 1 cell input and output in 1 cell.
P→L Given presentation, show links.
P→U Given presentation, show unity. Given symptoms/signs show diagnoses.
P→M Given presentation, show management.
L→P Given links, show presentation.
L→U Given links, show unity. Given abnormal test results, show diagnoses.
L→M Given links, show management.
M→P Given management, show presentation. Given treatment, show adverse symptoms/signs.
M→L Given management show links.
M→U Given management show unity. Given a single treatment, show diagnoses, that is a therapeutic index. However if there is more than one treatment, it will show adverse drug to drug interactions leading to diagnoses listed in unity cell.
U→P Given unity, show presentation. Given diagnoses, show symptoms/signs.
U→L Given unity, show links. Given diagnoses, show associated abnormal test results.
U→M Given unity, show management. Given diagnoses, show treatment.

Queries of the 1 cell input and output in 2 cells.
P→LU Given presentation, show links and unity. Given symptoms/signs show abnormal test results and diagnoses.
P→UM Given presentation, show unity and management. Given symptoms/signs, show diagnoses and management.
P→LM Given presentation, show links and management.
L→PU Given links, show presentation and unity. Given abnormal test results, show symptoms/signs and diagnoses.
L→UM Given links, show unity and management. Given abnormal test results, show diagnoses and treatment.
L→PM Given links, show presentation and management.
M→PL Given management, show presentation and links.
M→LU Given management show links and Unity. Given treatment, show abnormal test results and adverse diagnoses.
M→PU Given management show presentation and unity. Given treatment, show adverse presentation and diagnoses.
U→PL Given unity, show presentation and links. Given diagnoses, show abnormal test results and symptoms/signs.
U→LM Given unity, show links. and management
U→PM Given unity, show presentation and management Queries of the 1 cell input and output in 3 cells output.
P→LUM Given presentation, show links, unity and management. Given symptoms/signs, show abnormal test results and treatment.
L→PUM Given links, show presentation, unity and management. Given abnormal test results, show symptoms/signs, diagnoses and treatment.
U→PLM Given unity, show presentation, links and management. Given diagnoses, show symptoms/signs, abnormal test results and treatment.
M→PLU Given management, show presentation, links and unity.

Queries of the 2 cell input and output in 1 cell
PL→U Given presentation and links, show unity. Given symptoms/signs show diagnoses.
PU→L Given presentation and unity, show links. Given symptoms/signs and diagnoses, show abnormal test results.
PM→L Given presentation and management, show links
LU→P Given links and unity, show presentation.
LM→P Given links and management, show presentation.
MU→P Given management and unity, show presentation.
PL→M Given presentation and links, show management.
PU→M Given presentation and unity, show management. Given symptoms/signs and diagnoses show treatment.
PM→U Given presentation and management, show unity.
LU→M Given links and unity, show management.
LM→U Given links and management, show unity.
MU→L Given management and unity, show links.

Queries of the 2 cell input and output in 2 cells.
PL→UM Given presentation and links, show unity and management. Given symptoms/signs and abnormal test results, show diagnoses and management.
PU→LM Given presentation and unity, show links and management.
PM→LU Given presentation and management, show links and unity.
LU→PM Given links and unity, show presentation and management.
LM→PU Given links and management, show presentation and unity.
UM→PL Given unity and management show presentation and links.

Queries of the 3 cell input and output in 1 cell.
PLU→M Given presentation, links and union, show management.
PLM→U Given presentation, links and management, show unity.
LUM→P Given links, unity and management, show presentation.
UM→L Given presentation, unity and management, show links.

Examples of useful queries whereby output is redirected back to input cell.
PLU→U Given presentation, links and unity, show unity. In this instance the list of diagnoses in unity is cropped if they are not supported by the list of items in presentation and links.
P→P Given presentation, show presentation. Given symptoms/signs show more symptoms and signs that need to be elicited.
L→L Given links, show more links. Given abnormal test results, show more related abnormal test results.
U→U Given unity, show more unity. Given diagnoses, show more related diagnoses.
M→M Given management, show management. Given treatment, show more related treatment.

U M→U Given unity and management, show unity. Given treatment and diagnoses, show adverse diagnoses as a consequence of disease—drug or diseaseprocedure interaction.

Global Medical Appraisal

This basic tetrad model ( tetrad and PLUM used interchangeably) may be used for the encounter, global active and global inactive components of the medical record. In this way, a patient's health data can be comprehensively and effectively categorised for information entry and retrieval.

In this way, it facilitates efficient evaluation of the patient status with the consistent tetrad data model that is used for representing the data arising from a patient encounter. The PLUM data model is used for recording the patient encounter, is labelled the ENCOUNTER TETRAD. This same model is also used for the data representation of the patient's overall global health status termed the GLOBAL ACTIVE TETRAD. This information model of the patient data comprehensively classifies all clinical events occurring in patient care, and lends itself to easy computerisation. The functionality is improved over the old method in that instead of a problem list, the clinician gets a global situation report of the patient based on a matrix of four data categories that mirrors exactly the encounter model. Clinical events that are considered inactive are posted onto the GLOBAL ACTIVE TETRAD doppelganger called the GLOBAL INACTIVE TETRAD.

This consistent approach for both the local encounter and the global patient health status results in timely and easy accessibility and visibility of patient health status with the following tangible advantages: 1) avoidance of unnecessary pathology testing; 2) initiation of proper investigation of the patient; 3) improved evaluation of patient with early diagnosis; and 4) improvement in patient management in terms of therapeutics and appropriate procedures.

In this embodiment, the deliberate strategy is to move all exceptional or important clinical data that may have a future significance to the GLOBAL ACTIVE TETRAD. In a sense, the GLOBAL ACTIVE TETRAD is a "persistent encounter".

The problems of achieving an evaluation patient health model applicable for both the encounter notes (local level) and the general patient status (global level) and the doctor/machine interface problem are also met. This evaluation oriented multi-phasic (the phases being encounter, global active, global inactive and global log PLUM) tetrad model of patient health data is equally suited for both the manual or electronic medical record and combination thereof.

An important feature of this embodiment is an identical data model for the encounter notes and in depicting general patient status. This model works well in the fully manual mode. In the hybrid manual/electronic record system, the respective strengths of both the manual and electronic versions of the medical record are utilised. In the hybrid system, the paper medical record based on this health model can be inputted by scanning and in that way is seamlessly integrated with its electronic equivalent. Alternatively, the system can be used in a predominantly electronic way. Input into the electronic record can then be effected by keyboard, voice recognition or by a pen/graphic tablet device.

Pen device with a writing tablet and handwriting recognition software combination is available in the marketplace already (eg Fujitsu Script 1000). In the latter case, a hard copy of these notes can be printed out by the computer system to be included in the manual record if needed.

To answer the clinical question, what in a nutshell is the overall clinical status of the patient? Instead of a problem list in the old medical record system, the global patient status is represented by the GLOBAL ACTIVE TETRAD which contain the persistent elements of the PLUM matrix comprising Presentation, Links, Unity and Management. This is like having a running score sheet on the patient clinical status. With patients being looked after by multiple doctors, this running score sheet or snapshot of the patient health status is a powerful tool to achieve good health worker to health worker communication.

The GLOBAL ACTIVE TETRAD may, for instance be used to get answers to the following questions when the consultation commences by looking at the appropriate category in the GLOBAL ACTIVE TETRAD.
1) What has been the past diagnoses?
   Answer: Look up Global Active Unity
2) What are the persistent symptoms/signs?
   Answer: Look up Global Active Presentation
3) What tablets is the patient on?
   Answer: Look up Global Active Management
4) Is this patient still on physiotherapy?
   Answer: Look up Global Active Management
5) Are there any abnormal test results to worry about?
   Answer: Look up Global Active Links
6) Is the patient allergic to penicillin?
   Answer: Look up Global Active Unity
7) Is there a periodic test for this patient on warfarin?
   Answer: Look up Global Active Management.
8) When was the last fill blood examination done?
   Answer: Look up Global Inactive Links.

The PLUM Layout of the Clinical Encounter Form—Manual Version

The layout model of the clinical encounter form is an external embodiment of the concept behind the tetrad model. There are five columns in the encounter sheet. The first column is for the date of consultation, the second column is for Presentation, the next for Links, the next for Unity and finally the last column for Management events. This organisation on a paper such as A4 with a landscape page layout is economical. More importantly the functional benefit is the ease for the eyes of the clinician to scan up and down for the medications he has prescribed, the tests he has done in the management section and the results of his investigations in the links section. This layout of data categorises the data of the TETRAD along a horizontal axis and chronologically sort the events on a vertical axis.

The Hybrid Medical Record

The clinician records his encounter notes in the encounter form. It is recommended that he uses an alphabetic medical coding system such as the DOCLE notation/classification/coding system to facilitate computer representation of health data. The clinician enters the date and proceeds to log the events in the respective presentation, links, unity and management sections. The doctor can update any persistent or significant clinical events such as chronic diseases and allergies in the GLOBAL ACTIVE TETRAD form. to raise consciousness of important clinical events that will impact on subsequent consultation and management. This encounter form can then be scanned into the electronic medical record. The encounter form has rectangular boxes for Presentation, Links, Unity and Management. Inside each rectangular box, the context of the box is set by the key word in the upper left hand corner of the box. Computer recognition of handwriting has made great stride, eg the Apple Newton and Fujitsu Script 1000. The program can then transform the handwritten text into ASCII text which can then be used to update the electronic medical record.

The Fully Electronic Medical Record

The encounter form has an option in Utility Menu to post any event in GLOBAL ACTIVE TETRAD or GLOBAL INACTIVE TETRAD or both. The GLOBAL ACTIVE TETRAD comprises four list boxes which is scrollable. The events held in the list boxes are chronologically sorted.

Any selection made in the list box can be toggled from active to inactive and vice versa. This separation of global events into foreground (active) and background (inactive mode) is a form of exception reporting and is a useful feature of this record system.

The PLUM Based Legal Spreadsheat

The legal spreadsheet is based on the above data model and methods. It uses the same Graduated Discrete Definition Model to model the legal status of a client . The classification of legal data is based on the criterion of degree of definition in terms of readiness for legal judgement and subsequent court remedies. Utilising the same terminology, on one end of the spectrum, the not-yet-defined or Presentation data in law, comprises attributes that describe but not fully resolve the legal problem. Examples of Presentation are: land purchase, dispute over fishing rights, marital disagreement, neighbourhood dispute etcetera.

At the other end of the spectrum, with respect to the law, we have the well-defined legal principles which when proven will force the issue with respect to a final judgement and subsequent court order. The well defined legal principles or legal truths of common law and the specific sections of statute laws are collectively equivalent to the concept of diagnosis in clinical medicine. There may be one or more intermediate categories positioned between the not-yet-defined and the well-defined categories. One preferred option of this legal spreadsheet has only one intermediate category called the about-to-be-defined category. In the legal equivalent, this about-to-be-defined category called Links, comprises precedent legal cases. So in the belief system model constructed for the legal spreadsheet, the legal precedents are the logical equivalent of laboratory test results.

The tetrad version of the Graduated Discrete Definition Model called PLUM which, as mentioned above, stands for Presentation Links Unity Management. Using this terminology, all legal data to describe the client status are classified into the four categories of : 1) Presentation—this comprises all Not Yet Defined legal data that are unresolved attributes of the case. 2) Links—this comprises all About To Be Defined legal data, which by definition are the precedent legal cases which pave the way to a legal diagnosis. 3) Unity—this Well Defined legal data comprises the legal principles or truths enunciated by the judges in their reasoning and judgement or equivalent statute laws. 4) Management—this comprises the actions of the court after having coming up with a judgement—the contract may be 34 nullified, or other remedies may be prescribed by the judge. The legal spreadsheet encounter form has four cells, each representing the four categories of PLUM.

The Presentation cell is reserved for Not Yet Defined legal data. The Links cell is reserved for About To Be Defined legal data or precedents. The Unity cell is reserved for Well Defined legal data. The Management cell is for legal data related to court prescriptions or remedies.

The tetrad PLUM of the Graduated Discrete Definition Model provides the logical framework for the spreadsheet. This tetrad model is congruent with the underlying logic of the medical/legal process which is the processing of unclear medical/legal information to resolution in the clinical encounter or adversarial law court, resulting in a finding for one of the parties by the judge based on a sound legal principle or the equivalent of a medical diagnosis. An appeal to a higher court being nothing more than the equivalent medical situation of a patient asking for a second opinion. While the medical specialist orders more tests, the lawyer orders more reviews of precedent cases.

The Graduated Discrete Definition Model resolves the aforementioned incongruities of the traditional legal paradigm and classifies all legal data into these neat and mutually exclusive categories. The modelling of legal data in this manner lays the foundation for the construction of the legal spreadsheet and its powerful query language. The design of the legal spreadsheet obviates the need for the lawyer to type as there is a comprehensive pick list with search facility not withstanding current developments in speech recognition. A brief list of queries, with the equivalent medical queries in parentheses, demonstrate the commonality of problem solving in medicine and law:

a) Given Presentation, show Links.
   (Given symptoms and signs, show associated abnormal tests)
   (Given attributes, show legal precedents)
b) Given Unity, show Management
   (Given diagnoses, show treatment)
   (Given legal diagnoses, show legal remedies).
c) Given Unity, show Presentation and Links
   (Given diagnoses, show symptoms and signs and abnormal tests).
   (Given legal diagnoses, show attributes and precedents).
d) Given Management ,show Unity and Links
   (Given treatment, show adverse diagnoses and abnormal test results arising from treatment)
   (Given a court remedy eg contract@nullify, show legal diagnoses and precedents)
e) Given Unity, show more Unity.
   (Given a list of diagnoses, infer a further diagnosis that might unite several diagnoses)
   (Given a list of legal diagnoses, recruit more legal diagnoses—in many precedents, the decision may be based on several legal principles)
f) Given Presentation and Unity, show Links.
   (Given symptoms and signs, and diagnoses, show abnormal tests that explain findings)
   (Given attributes of the case and the legal diagnosis—show precedents that conform)
g) Given Links, show Unity
   (Given a abnormal laboratory or radiological result, what are the diagnoses)
   (Given precedents, what are the legal diagnoses)
h) Given Presentation, Links and Unity, show Unity.
   (Given a list of diagnoses, prune those diagnoses that do not have the listed symptoms, signs and laboratory results).
   (Given a list of legal diagnoses, prune those diagnoses to conform to the listed attributes and precedents).

A more comprehensive list of legal queries is dealt with in the detailed section.

The output of the evaluations are into the cells, and are ranked on the basis of probability. The legal spreadsheet enables critical computer evaluation of the client legal status. The legal spreadsheet is designed to be used in an iterative manner for solving legal problems. As a result of each query, the cells are updated, the user can choose to edit the cells and a further query can be launched.

Each cell is a text pane or list box, for the evaluation exercise, having only the first word of each new line parsed, is efficient. This design allows the lawyer to enter free text to augment his notes. Practical output of the spreadsheet includes 1) a print out of the legal status as defined by the four categories; 2) an ordering of the list of legal precedents that the lawyer will have to do research on; 3) the list of target legal diagnoses that the lawyer will want to impart or influence on the judge for use in his judgement.

Like the medical situation, legal data can be further classified beyond the four levels of 1) not-yet defined; 2) about-to-be-defined; 3) well-defined; and 4) Management. This leads to a screen with additional cells due to the increased number of categories. The preferred option is to keep the application simple for the user. Hence the four cells of Presentation, Links, Unity and Management appear to be an efficient solution.

In one form of the invention, the spreadsheet functions as a stand alone program, there is no note-taking capacity and the cells are implemented as list boxes. In the stand alone mode the spreadsheet is a library resource, a legal tutor and is excellent for sharpening the skills of the law student using the spreadsheet in a discovery mode.

This new metaphor in medical and legal problem solving means that the problem can be approached from top-down or bottom-up or with a middle point entry as the spreadsheet works with categories of not-yet-defined data, about-to-be-defined data and well-defined data.

Traditionally, law is classified in the following and overlapping manner.

As sources of law:
  a) Statute law
  b) Common law

As source of person bringing the action
  a) civil law—the plaintiff brings on the action
  b) criminal law—the state or crown is the prime mover Then these are the major overlapping categories conforming to specialities traditionally identified by the legal profession as:
  a) tort—anything actionable but not crime or contract
  b) contract
  c) criminal law
  d) intellectual property law
  e) consumer law
  f) family law
  g) business law etc.

Looking at a legal text book from chapter to chapter, precedents are intermixed with legal concepts. Precedents involving several conflicting legal principles are lost among several chapters. The relationships among these entities are fuzzy and not easily amenable to computer evaluation.

As stated above the Graduated Discrete Definition Model reworks the old legal model to make it homogenous enough to be amenable to computer processing. In such a model, a legal data item belongs to one and only one category. In the tetrad version of the GDDM, the Presentation category covers all legal data except legal precedents, legal principles of the Unity category and legal remedies. The Links category covers all legal precedents. The Unity category covers all legal principles that are defined to the level suitable for use as a justification device in legal judgement. While the Management category covers all legal remedies, prescriptions and sentencing. If we care to look at the typical client-lawyer interaction, the client presents a narration of his legal problem, the lawyer refers to and recruit analogous precedents which provide important legal principles which if accepted by the judge might favour his client—the legal data has moved from being "not yet defined" to "about to be defined" to being "well-defined" for convincing the judge. A putative legal judgement or well-defined state is reached, it is then that prognostication is given to the client about the probable judgement and legal remedy that will likely be prescribed. The data flow of the legal process is of the following nature:

NOT YET DEFINED legal events→ABOUT TO BE DEFINED legal events→WELL DEFINED legal events→LEGAL REMEDY Or in the parlance of the PLUM model:

Presentation→Links→Unity→Management

But often the flow of data is iterative when diagnosis is not obvious,

Presentation→Links→Unity→Links(precedents) etc.

The cascade of events flow logically from ill-defined events to intermediate-defined events to be followed by well-defined events which then trigger treatment and the proffering of prognostication. Therefore the legal event descriptor that is unclear enough for the lawyer to prescribe treatment or offer prognostication, is classified as NYD or "Not Yet Defined". On the other hand, if the legal event is a clear legal principle (diagnosis) that is well defined enough for specific legal remedy and therefore allowing clear prognostication to the client , then the legal event descriptor is classified as WD or "Well Defined". To recapitulate, all legal event descriptors that are used to describe client status fall into one of the four mutually exclusive categories of Presentation (Not Yet Defined), Links (About To Be Defined), Unity (Well Defined) and Management (legal remedies). Sitting underneath these four categories is a legal coding and classification system based on the Linnean system. The four categories of the PLUM tetrad model constitute the four phyla of this Docle-L classification system. Not only are legal data classified into the four phyla of Presentation, Links, Unity and Management. Each legal species which belong to one of the above phylum are classed in a linnean manner with memberships in class, order family and genus.

Docle-L Legal Coding And Classification—a high level language representation of legal data.

The legal classification system with its four phyla is the "glue" that makes the legal spreadsheet possible, without this "glue", the spreadsheet project will fall apart. Docle-L is alphabetic, as opposed to the alternative numeric type coding and classification system. Numeric coding systems to represent legal data are too complex for the programmer to work with. The Docle-L legal coding and classification system used in the legal spreadsheet package has been designed to solve the following problems 1) a coding system in legal informatics 2) a legal belief system that parallels the Linnean model in biology suitable for the organisation of legal knowledge and 3) a legal belief system suitable for the design and implementation of sophisticated legal decision support systems and 4) an abbreviation system for legal terms. The Docle-L classification system has drawn the two strands of biology and law together in that they follow the Linnean model of classification. With the Docle-L system, legal entities are classified the way biologists classify plants and animals. Swedish scientist Carolus Linnaeus in the 1750s introduced the binomial nomenclature for species and is generally regarded as the father of modern taxonomy. The seemingly impossible task of classifying legal cases and legal principles using this same Linnean model has been solved by the application of three concepts that are widely known in computer science—subclassing, multiple-inheritance and object programming.

In biology, a congruous classification system exists in the form of the Linnean model. The Linnean model forms the basis of a belief system that dynamically changes with the growth of biological knowledge. There does not exists a coding problem in the field of biology because of the strict discipline of the binomial nomenclature. If in the field of law, we can develop a framework equivalent to the biological model, to represent the state of knowledge in law, we would solve the law coding and classification problems in one fell swoop.

The Docle-L law classification system draws the two strands of biology and law together to follow the Linnean model of classification. Legal entities are classified the way biologists classify plants and animals. The lessons from the history of computing indicates a trend to move away from numeric coding to a higher level language coding.

The whole realm of legal objects is classified into phyla or chapters. The main categories of the tetrad model proposed in the construction of this legal spreadsheet is represented at the phylum level of this classification. The phyla are 1) Presentation—attributes 2) Links—legal cases 3) Unity—legal principles defined to a level enabling the basis of judgement and 4) Management—legal remedies and prescriptions.

Docle-L nomenclature fulfils the role of the Latin binomial nomenclature of the Linnean model. It is a structured legal language with unparalleled power of expression. Docle-L terms are built up using operators. For example the legal principle of mistake in a contract associated with the concept of res sua is written as contract@mistake@resSua. The @ operator translates to "apropos". A controlled lexicon is then constructed, the root terms are recycled thereby creating an efficient small kernel of terms. This unique Docle-L expression becomes a key to a Docle-L object (see example later).

A very useful concept in Docle is that of primary, secondary and tertiary keys. Using the example of the contract@mistake@resSua object, the primary key is contract@mistake@resSua, the secondary key which is computer generated is contract@mist@ress, the tertiary keys are the aliases for the legal object to provide alternate access, in this instance the alternate keys may be 1) theThingWasAlreadyHis 2) resSua. The essential point being all keys are equal in the sense that they all lead to the same contract@mistake@resSua object.

In addition, there are possibilities of variations to the above legal object—there may be subspecies of contract@mistake@resSua: contract@mistake@resSua@unilateral and contract@mistake@resSua@bilateral—that is why we need to go "biological classification" as there are so many variations on the same theme being played out in the courts.

With this approach, the building of controlled synthetic expressions using basic terms and operators to represent the abstruse legal concepts becomes a feast in verse.

Docle-L makes use of the concept of separation of data from the key itself This deferment of data binding to the key provides Docle-L with unparalleled flexibility to expand and mutate with the growth of legal knowledge. The key, be it primary, secondary or tertiary-all leads to the same legal object with its stored behaviour. Advances in law will lead to gradual adjustments to the behaviour of the legal object. It is hard to envisage the need to change species names such as contract@mistake@resSua or contract@mistake@resExtincta. The key to the concept is constant, but the legal remedy may mutate over time, even the definition of this event may change—with this classification the key is always separate from the object it represents (in computer terms, the key is a name of a computer variable instead of a computer constant).

As law informatics mature over the coming decades, the demand will be for systems that help in legal evaluation of client problems. In such a decision support system, there must be a plinth for the inference engine to work properly. The artificial intelligence community refers to this as a belief system. A collection of lists of number codes is not a congruous belief system that can sustain a modern electronic legal decision support system. The biological classification is a plausible belief system. We can discover a new species today and match it to the nearest genus, give it a Latin sounding species name and presto, the problem is solved.

The challenge then is to come up with a viable belief system for organising the spectrum of legal entities. One that is as stable and elegant as the Linnean model.

Overview of the Docle-L Classification

Law informatics has not made significant progress with the lack of an efficient coding and classification system.

The problem is that a mature computer and scientific classification of legal entities does not exist. This is so, in comparison with the well developed and disciplined biological classification system. Lawyers have failed to come up with a set of species names for legal entities. We have failed to define the concept of a legal species. Hitherto there are no legal equivalents for the phylum, class, order, family and genus of biology. There is no equivalent binomial nomenclature in law. The lack of emphasis on legal species identification, and the attendant lack of standardisation of species names is of course due to the absence of a congruous framework in law. The rapid development of jurisprudence and the critical lack of a decent classification framework for the law has resulted in a fragmented state of affairs. We have huge islands of information held in libraries and on-line electronic databases. A classification system such as Docle-L has the means to put all that legal information into a congruous framework.

Instead of coming up with more key word searches and linkages to sort the massive electronic databases, the challenge is to create an equivalent Linnean system whereby outmoded and illogical legal precedents are left out of the main Docle-L belief and classification system. We are not yet proposing Latin binomial nomenclature. But it is a thought. To implement the Docle-L classification system, there are three prerequisites. Firstly we need the equivalent of the binomial nomenclature. This nomenclature must be a powerful and standard way of describing legal entities. Secondly, we need to completely rework the Linnean hierarchical levels and introduce new definitions for the various levels. Thirdly, we need to create new rules for the classification process. Instead of Latin names, we have a structured legal descriptive language called Docle-L. In the majority of cases, Docle-L names are names of legal entities that are straight out of the legal textbooks. Often they may look like someone's internet addresses.

The direction that Docle-L has taken is to use the concept of the species name as the KEY to a legal object, also called a Docle-L object. Hence Docle-L is a classification of legal objects. This classification of legal objects is also called Objects Lex. The legal object holds information that refers to memberships of taxa, pointers to species in lower levels of hierarchy and its own level of hierarchy. That way as the study of law progresses, the legal object is updated but the key remains stable. As there is no need to assign numbers to entities that are not numbers, species names are alphabetic. The task is therefore clear 1) We have to identify all the species (or subspecies thereof) of legal objects—which are legal attributes, precedents, legal principles and legal remedies. 2) Assign to each species named, an object which is a data repository regarding its memberships of taxa and other information and 3) Classify them into a logical framework satisfying the requirements of all manner and types of legal workers. This is important as the legal coding systems must be designed for all the stake holders including students, lawyers, government, statisticians and certainly not only for the information scientist who is developing applications such as legal decision support systems.

The Docle-L Classification Framework

Present day biological classification is based on the work of Linnaeus in the 1750s. One of the central tenets of biological classification is the concept of the species. The other tenets being the hierarchies and the concept of the taxon (plural taxa). A taxon is a group with shared values in each hierarchy. Species identification is half the work, while the other half involves placing the species in the right taxon in the right hierarchy.

The Docle-L Classification system identifies the concept of a legal species. The legal species belonging to the Unity phylum is a unique legal principle that is defined to a degree that is suitable for use as justification of a legal judgement. It has well known features and has instances of the type precedents to demonstrate this principle, thereby there exists a predictable outcome for cases demonstrating this legal principle. A particular section of a statutory law is also a legal species. In theory, a legal diagnosis at the species level or better is required for specific legal remedy. This classification classifies all the legal species in a linnean type framework. As legal precedents are mere instances of legal species, all precedents are classified along the same manner as species. All precedents belong to the phylum Links.

The system of classification in Docle-L is based on the above framework with major modifications. It would be fair to say that Docle-L is the offspring of Linnean classification, object oriented programming paradigm and the subject of law. Whilst the concepts discussed were first implemented in an object programming environment, there is no problem whatever for Docle-L to be a manual system or written up in any standard database or high level computer language.

The main deviations from the Linnean model are
1) There can be more hierarchies defined below the species level. There are the subspecies, subsubspecies subsubsubspecies and subsubsubsubspecies levels definitions that are possible to cater for the many variations of a theme in law.
2) A species or any of its subclasses or instances can have membership in any number of taxa at any level. This is the multiple inheritance feature of Docle-L. For example a precedent may involve the classes of contract, tort and crime. A precedent or legal case might demonstrate more than one legal principle concurrently akin to a patient with multiple diagnoses.
3) The corollary of the above is that a species may have no membership of any taxon at any level. While missing links are abhorrent in biological classification, Docle-L works on the assumption of having missing memberships in certain hierarchies.
4) As implemented in Docle-L, a taxon knows its membership. A species knows who its phylum, class, order, family, genus, subspecies, subsubspecies, subsubsubspecies and subsubsubsubspecies are, if it has one or more.
5) The taxa at the next level down of the hierarchy does not need to be descendants of a taxon at the current level.
6) The entity to be classified is held in a Docle-L object (also referred to as a legal object), the name of the object becomes the key to the object. There are three types of key to these Docle-L objects. The primary key is the complete key that can look like a textbook name or an expression that looks like an internet address. Example of a primary key is contract@mistake@resSua. Note the absence of a space between the terms. The secondary key is computer generated from the primary key using an abbreviating algorithm. In this instance the secondary key is cont@mist@ress. The tertiary keys are the nominated aliases of the entity—resSuaContract and the ThingIsAlreadyHis.

The Hierarchies in Docle-L

1. Kingdom—there is only one taxon located at this hierarchy. It is named Objects Lex. Objects Lex holds all legal objects and all objects of legal thought.
2. Phylum—the four taxa are:
   a) Presentation—legal entities that are not Links, Unity or Management.
   b) Links—the precedents
   c) Unity—legal principles defined and utilised for judgement and the specific section of a statute
   d) Management—the legal remedies
3. Class—the taxa are the various legal specializations. A species may belong to one or more classes.
   a) contract
   b) criminal
   c) torts
   d) family
   e) commercial
   f) international
   g) municipal
   h) constitutional
   i) industrial
   j) administrative
   k) taxation
   l) intellectualProperty
   m) consumer
   n) property
   o) workersCompensation
   p) accident
   q) evidence
   r) procedure
   s) succession
   t) environmental
   u) social
4. Order—the sources of law: the taxa are common, statutes, equity, admiralty, ecclesiastical, judge@source, law@unitedStates, law@canada, law@international, law@australia, law@australia@native, law@australia@victoria, law@canada@victoria etc. A particular law species may have multiple sources of law and hence belong to several orders—eg Australian Trade Practice Act is modelled on United States law.

5. Family—the taxa are named after the major pieces of legislation or in the event there exists no statutes then the taxon common is used. Examples of this hierarchy are a) familyLawAct1975; b) tradePracticesAct1974; c) transportAccidentAct1986; d) indianContractAct1857.
6. Genus—a taxon at this level is a concept in law.

A concept at this level is not good enough for judgement and precise legal remedy.

Examples are: murder, defamation, indictable, summary, negligence, procedure@law@civil, procedure@law@criminal Examples of Genera from contract law are:
offer, acceptance, consideration, revocation, rejection, mistake, mistake@unilateral, mistake@mutual, intentionToBeBound, capacity, privity, contents, impliedTerms, misrepresentation, duress, undueInfluence, contract@voidable, contract@discharge, contract@illegal.

8. Species—The root word is the Latin specere which means to look at. At the species level the legal principle is defined to a degree sufficient enough for the judge to look at and make a judgement on the case based on the principle and prescribe a precise legal remedy. The species is often a finer restatement of an entity belonging to the genus level, eg murder@first@degree. This principle may be a section from statutory law. A species belonging to the phylum Unity is a characteristic legal principle with features generally well known by lawyers. Often there is knowledge about related precedents which are consonant with this legal species, thereby there exists a predictable outcome or prognosis for cases demonstrating this legal principle. In theory, for justice to be done, a legal diagnosis, by the jury/judge, at the species level or better is required before appropriate and specific legal remedy is prescribed.

Examples of species are contract@mistake@resSua, contract@mistake@resExtincta

The role of court precedents and its relationships in the Docle-L classification system Precedents belong to the phylum Links. A precedent is also an instance of a legal species. The analogy is Joe Blow is an instance of the species homo sapiens. We can learn a lot about homo sapiens by studying instances of homo sapiens.

A case study is that of a Links species—a precedent that is itself an instance of the Unity species known as contract@mistake@resSua.
name: cooperV.phibbs1867
kingdom: objects lex
phylum: Links
class: contract
order: common
family: nil
genus: contract@mistake mistake mistake@common
species: contract@mistake@resSua Docle-L nomenclature The first core concept of Docle-L is an algorithm that converts a piece of real world legal vernacular into a standard abbreviation. For example caveat emptor is repackaged by the Docle algorithm as caveatEmptor before it maps to the Docle word cavee. Note that Docle-L abhors the space character between words, the first word starts off as lower case while subsequent words start off with an upper case character. In the case of single word expression, the Docle product is the first four characters of the source word. In the case of a two word expression, the product is the Docle of the first word concatenated to the first character of the second. For the case of three or more word expression, the Docle result is the concatenated string of the first characters of each word. The second core concept is that of operators. Docle words can be combined together to form any number of complicated expressions by combining Docle terms with operators. For example the concept of mistake in contact can be expressed as contract@mistake—the @ operator translates to "apropos". Likewise the concept of mistake in evidence law can be expressed as evidence@mistake . The implementation of such a system must also cope with a) avoiding synonymous expressions b) mapping conflicts. The third core concept of Docle is that each of these unique Docle expressions becomes a key to a Docle object. The Docle coding engine is efficient for generating unique and meaningful codes. Docle is human readable and is more suited to input validation. For mission critical tasks, the lawyer must be able to visually vet for the correctness of computer data. Docle is intuitive and suitable for a unified legal abbreviation standard, for example; cont@mist means contract apropos mistake—that's intuitive.

Operators

The Docle operators are designed to give the Docle language the power of expression not seen with numeric coding of data. The operators allow the user to combine two or more Docle words together to form Docle expressions. Complex expressions are derived from the use of multiple Docle words and operators. Another operator is the V. or "V dot" operator which sits between the plaintiff's and defendant's names, denotes the precedent case. An example showing the coding for a multidimensional entity is contract@mistake@resSua. Often a legal determination is arrived at following a resolution of a conflict of two or more principles. More complicated expressions can be constructed using these operators:
>implies greater than
<implies less than
In the case of
mcRaeV.CommonwealthDisposalsCommission is an instance inherited from two Unity species,
contract@mistake@resSua
contract@mistake@resSua<contract@warranty@implied In the above case, the principle of implied warranty on the government's side of the bargain exceeds the principle of res sua, hence McRae could recover costs.

Docle-L classifies all legal objects into the four phyla of Presentation, Links, Unity and Management. A species of the phylum Unity is a legal principle that is defined to a level suitable for use as a basis for judgement. Specific and appropriate legal remedy is possible only when a legal diagnosis by the judge at the species level is made. A particular section (or chapter and verse) of a statutory law is also a Unity species. Precedents are defined as instances of such a species. Precedents are classified as the Links category. Management is the category that holds all legal remedies and prescriptions. Anything not classified as Unity, Links or Management is lumped into the Presentation category. This classification as defined has great pragmatic significance in the implementation of the legal spreadsheet.

The proper and logical classification of legal entities should follow the progress of law closely. A worthwhile classification system must be able to cope with new knowledge and constant change in the legal environment. A worthwhile legal classification should be a road map for the law profession, pointing the way to terra incognita. It is hard to read a road map comprising of numbers. The allocation of numbers to legal entities is always problematic as there is too much arbitrariness, too much thinking involved in number selection. Every effort should be concentrated on classifying, not on the process of linking to numbers to achieve a practicable spreadsheet.

Docle L Listing

Practical examples of legal entities coded in Docle-L with primary and tertiary keys mapped to secondary keys.
abandonmentContract cont@aban
abandonmentContractImplication cont@aban@implicat
acceptance acce
acceptance@conditional acce@cond
acceptance@email acce@emai
acceptance@fax acce@fax
acceptance@inference acce@infe
acceptance@means@stipulation acce@mean@stip
acceptance@mode acce@mode
acceptance@post acce@post
acceptance@revocation acce@revo
acceptance@telegram acce@tele
acceptance@tender acce@tend
acceptance@waiver acce@waiv
acceptance who acce@who
accord satisfaction acco@sati
agent authority agen@auth
aRobertsV.leicestershireCountyCouncil arv.lcc
aTestCase atc
attainted capa@atta
auctionBid bid@auct
averayV.Iewis lewiv.aver
bailment@consideration bail@cons
bellV.IeverBros bellv.leveb
bid@auction bid@auct
breach brea
breach@actual brea@actu
breach@agreement@exGratia brea@agre@exg
breach@clauses@exemption brea@clau@exem
breach@conditional brea@cond
breach@damages brea@dama
breach@promise brea@prom
breach@specificperforrnance brea@specp
breach@type brea@type
breach@warranty brea@warr
brooksV.phillips philv.broo
butcherV.solle soliv.butc
cameronV.pukallus pukav.came
capacity@alien capa@alie
capacity@attainted capa@atta
capacity@bank-rupt capa@bankrupt
capacity@conv-ict capa@convict
capacity@corporation capa@corp
capacity@drunk capa@drun
capacity@mental@ill capa@ment@ill
capacity@minor capa@mino
capacity@suiJuris capa@suij
capacity@woman@married capa@woma@marr
caveatEmptor cavee
cecilV.webster websv.ceci
colinAndShieldsV.hartog hartv.cas
commonwealthDisposalsCommission mrv.cdc
consideration@discharge cons@disc
consideration@doctrine cons@doct
consideration@exec-uted cons@executed
consideration@exec-utory cons@executor
consideration@forbearance@sue cons forb@sue
consideration@moralObligation cons@morao
consideration@past cons@past
consideration@public@duty cons@publ@duty
consideration@sufficiency cons@suff
consideration@valu-able cons@valuable
contract@abandonment cont@aban
contract@abandonment@impl-ication cont@aban@implicat
contract@abandonment@lapse cont@aban@laps
contract@adhesion cont@adhe
contract@bilateral cont@bila
contract@collateral cont@coll
contract@cond-uct cont@conduct
contract@crime cont@crim
contract@deed cont@deed
contract@defective cont@defe
contract@form cont@form
contract@form-ation cont@formatio
contract@frustration cont@frus
contract@illegality cont@ille
contract@privity cont@priv
contract@sale@business cont@sale@busi
contract@sale@property cont@sale@prop
contract@seal cont@seal
contract@service cont@serv
contract@simple cont@simp
contract@unconscionable cont@unco
contract@unilateral cont@unil
contract@verbal cont@verb
contractBreach brea
convict@capacity conv@capa
cooperV.phibbs coopv.phib
copyright@assignment copy@assi
counter-offer counoffe
couturierV.hastie coutv.hast
cross-offers crosoffe
cross-offers@effect crosoffe@effe
cundyV.lindsay cundv.lind
delegatusNonProtestDelegare dnpd
deMinimisNonCuratLex dmncl
dennyV.hancock dennv.hanc
eiusdemGeneris eiusg
exAntecedentibusEtConsequentibusFitOptimalnterpretatio eaecfoi
expressioUniusEstExclusioAlterius eueea
exTurpiCausaNonOritorActio etcnoa
fullLegalCapacity capa@suij
gallowayv.galloway gallv.gall
goldsbroughMortV.quinn gmv.quin
hartogV.colinAndShields hartv.cas
hindleyV.scrivenBros sbv.hind1913
holtV.markham holtv.mark
hughesV.smith smitv.hugh1871
idCertumEstQuodCertumReddiPotest iceqcrp
ignorantiaJurisHaudExcusat ijhe
inPariDelictoPotiorEstConditioDefendentis ipdpecd
interestReipublicaeUtSitFinisLitium irusfl
jamesV.tamplin tampvjame
johnsonV.taylor taylvjohn
joscelyneV.nissen joscv.niss
kingsNortonMetalV. eldrigeMerritt knmv. eldrm
leicestershireCountyCouncilV.aRoberts arv.lcc
leverBrosV.bell bellv.leveb
IewisV.averay lewiv.aver
lindsayV.cundy cundv.lind
locusPoenitentiae locup
markhamV.holt holtv.mark mcRaeV.CommonwealthDisposalsCommission mrv.cdc
nissenvjoscelyne joscv.niss
norwichUnionFireInsuranceSocietyV.williamHPrice nufisv.whp
offer offe
offer@acceptance offe@acce
offer@advertisement offe@adve
offer@auction offe@auct
offer@bid offe@bid
offer@catalog offe@cata
offer@counter-offer offe@counoffe
offer@death offe@deat
offer@hire@purchase offe@hire@purc
offer@intention offe@inte
offer@invitation offe@invi
offer@knowledge offe@know
offer@lapse offe@laps
offer@mistake offe@mist
offer@puff offe@puff
offer@rejection offe@reje
offer@revocation offe@revo
offer@shop offe@shop
offer@world offe@worl
ornisRatihabitioRetrotrahiturEtPrioriMandatoAequiparatur orrepma
paulV.riverlateProperties rpv.paul
phibbsV.cooper coopv.phib
phillipsV.brooks philv.broo
pimV.rose rosev.pim
potiorEstConditioDefentidis pecd
pukallusV.cameron pukav.came
quiFacitPerAliumFacitPerSe qfpafps
quinnV.goldsbroughMort gmv.quin
rafflesV.wichelhaus raffv.wich
resExtincta rese
resPeriitDomino rpd
resSua ress
riverlatePropertiesV.paul rpv.paul
roseV.pim rosev.pim
scriptumPredictumNonEstFactumSuum spnefs
scrivenBrosV.hindley1913 sbv.hind1913
smithV.hughes1871 smitv.hugh1871
solleV.butcher sollv.butc
strickiandV.Turner1852 striv.tum1852
tamplinVjames tampvjame
taylorVjohnson taylvjohn
turnerV.strickland striv.tum1852
utResMagisValeatQuamPereat urmvqp
verbaCharatarumFortiusAccipiunturContraProferentem vcfacp
vigilantibusNonDormientibusJuraSubveniunt vndjs
websterV.cecil websv.ceci
wichelhausV.raffles raffv.wich
williamHPriceV.norwichUnionFireInsuranceSociety nufisv.whp The implementation of the legal spreadsheet is based on the concept of objects and objects responding to messages— the Object Oriented Programming System paradigm. All the legal data in the tetrad model are objects and respond to messages. For example the Unity object of contract@mistake@resSua when sent a query message of list_Presentation will provide a list of attributes associated with legal precedents with the rulings based on res sua held in the knowledge base. The message of list_Links will list all the legal precedents associated with the legal principle of res sua. While the message list_Management will list the legal remedies for the legal principle of contract@mistake@resSua which will return a Management category species such as contract@nullify.

Method of operation for queries of the type:

P→U

This query reads as "Given Presentation show Unity". This is implemented by performing in series the queries P→L followed by L→U.

L→U

This query reads as "Given Links show Unity".
The program can interrogate all the Links objects for their legal diagnoses.

M→P

This query reads as "Given Management show Presentation".
This is derived from performing in series M→U, U→L and L→P

M→U

"Given management show unity". The program can interrogate all Unity objects and select those whose management equals M.

U→P

This query reads as "Given Unity show Presentation". The sequence is U→L and L→P.

U→L

This query reads as "Given Unity show Links". The program can interrogate all Unity objects to list all their associated Links.

U→M

This query reads as "Given Unity show Management". The program can interrogate all Unity objects to list all their associated Management.

P→LU

This query reads as "Given Presentation show Links and Unity". The sequence is P→L and L→U

P→UM

This query reads as "Given Presentation show Unity and Management". This is a powerful problem solving method. Effectively the sequence of 1) P→L 2)L→U 3)U→M.
If P was say contract@mistake then all possible legal diagnoses and legal remedies are noted. The next step is to edit the cells to choose the legal diagnosis and legal remedy you wish your client will have then use UM→L to show all the precedents that might help.

L→PU

This query reads as "Given Links show Presentation and Unity". This query is actually the following queries done in sequence 1) L→U 2) U→P.

L→UM

This query reads as "Given Links show Unity and Management". This query is actually the following queries done in sequence 1) L→U 2) U→M.

M→LU

This query reads as "Given Management show Links and Unity". This query is actually the following queries done in sequence 1) M→U 2) U→L.

M→PU

This query reads as "Given Management show Presentation and Unity". This query is actually the following queries done in sequence 1) M→U 2) U→P.

U→PL

This query reads as "Given Unity show Presentation and links". This query is actually the following queries done in sequence 1) U→P 2) U→L.

P→LUM

This query reads as "Given Presentation show Links Unity and Management". This query is actually the following queries done in sequence 1) P→U 2) U→L and 3) U→M.

L→PUM

This query reads as "Given Links, show Presentation, Unity and Management". This query is actually the following queries done in sequence 1) L→U 2) U→P and 3) U→M.

U→PLM

This query reads as "Given Unity show Presentation, Links and Management". This query is actually the following queries done in sequence 1) U→P 2) U→L and 3) U→M.

PL→U

This query reads as "Given Presentation and Links, show Unity". This query is actually the following queries done in sequence 1) P→U 2) L→U.

This is followed up by the collation and ranking of the U contents.

PU→L

This query reads as "Given Presentation and Unity, show Links". This query is actually the following queries done in sequence 1) P→U 2) U→L.

This is followed up by the collation and ranking of the L contents.

PU→M

This query reads as "Given Presentation and Unity, show Management". This query is actually the following queries done in sequence 1) P→U 2) U→M.

This is followed up by the collation and ranking of the M contents.

PL→UM

This query reads as "Given Presentation and Links, show Unity and Management". This query is actually the following queries done in sequence 1) P→U 2) L→U and 3) U→M.

PLU→U

This query reads as "Given Presentation, Links and Unity, show Unity". This query is actually the following queries done in sequence 1) P→U 2) L→U. The intersection of the sum of these two outputs and the original U contents gives the list of Unity objects consistent with Presentation and links. This query is useful to trim long lists of differential legal diagnoses.

P→P

This query reads as "Given Presentation show Presentation". This query is to query the Presentation objects to release more associated Presentation objects. The implementation details are: 1) P→U 2) U→P. A presentation object is used to recruit more associated presentation objects.

L→L

This query reads as "Given Links show Links". This query is to query the Links objects to release more associated Links objects. The implementation details are: 1) L→U 2) U→L. This query is useful for suggesting more precedents that are associated via presentation or unity characteristics.

U→U(max)

This query reads as "Given Unity show Unity maximised".

In the case of one Unity object, it queries the Unity object to release more associated Unity objects. One implementation is of the form: 1) U→L 2) L→U and 1) U→P 2) P→U. These sequences produce a longer list of legal diagnostic possibilities.

M→M

This query reads as "Given Management show Management". This query is to query the management objects to release more associated management objects. The implementation details are: 1) M→U 2) U→M.

UM→U

This query reads as "Given Unity and Management show Unity". This query is to shorten the list of Unity objects to conform with the given management objects.

BRIEF DESCRIPTION OF FIGURES

The invention will be further illustrated with reference to the accompanying drawings in which:

FIG. 1 is a medical spreadsheet based on the tetrad version of the Graduated Discrete Definition Model.

Four main cells labelled Presentation, Links, Unity and Management are provided. The pick list is on the right It contains a list of presentation objects. Superior to the pick list is a search pane and the 'Go' button to help locate the right medical object. The contents of the pick list can be altered by choosing any of the PLUM buttons sitting superior to the search pane.

Figure 1:
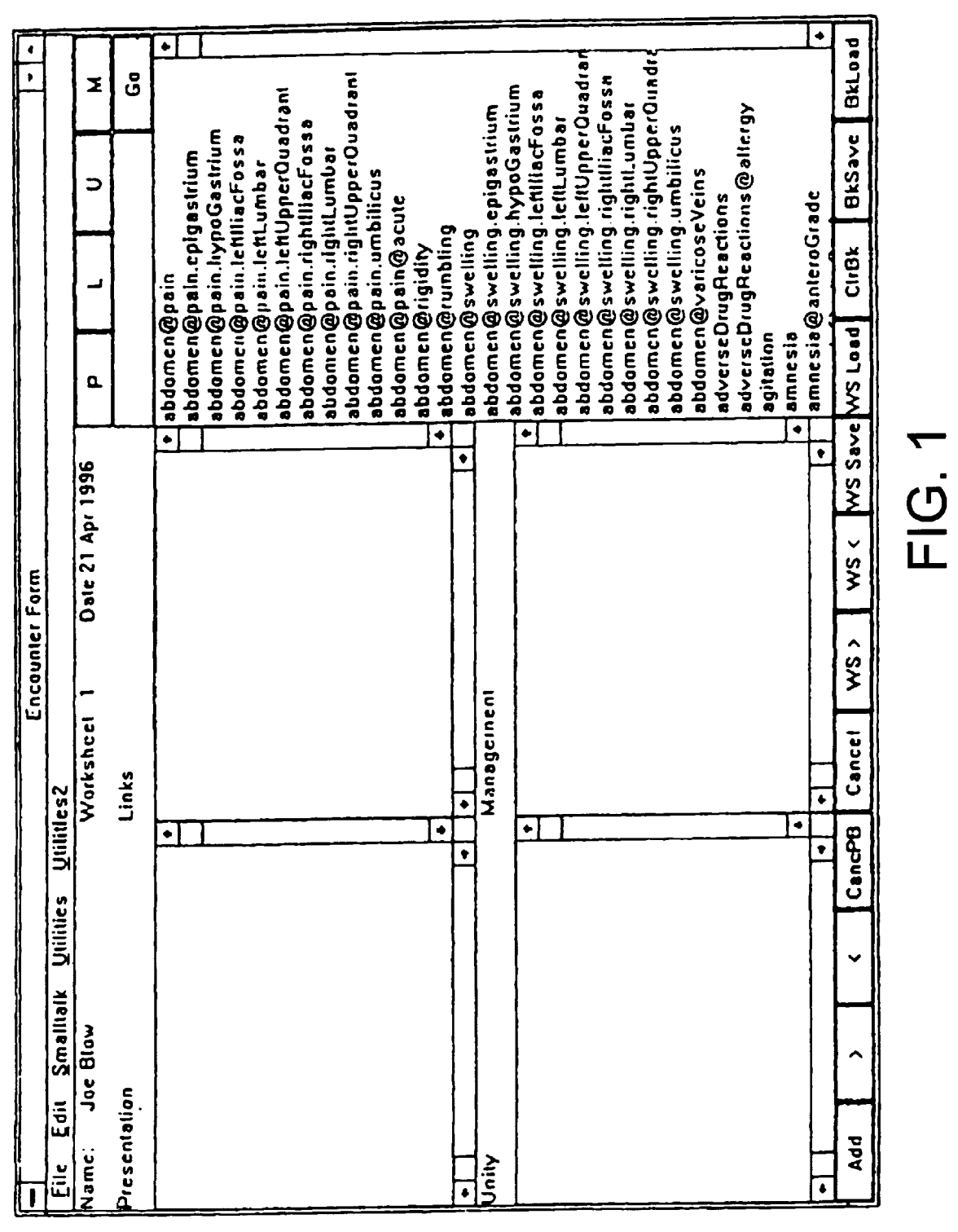

FIG. 2 is the spreadsheet of FIG. 1 with the cells having greater horizontal magnitude.

The buttons lined up along the bottom are 1) add—the encounter to medical record; 2)>is to forward to next encounter; 3)<is to go back to previous encounter; 4) cancPB is to cancel play back of encounters; 5) cancel is to get out of encounter, no update; 6) WS>is to scroll to next work sheet; 7) WS<is to scroll back to previous work sheet; 8) WS Save is to save a particular work sheet; 9) WS Load is to load a particular work sheet; 10) clrBk is to initialise all work sheets; 11) BkSave is to save all work sheets; 12) BkLoad is to load a previous collection of work sheets.

Figure 3:
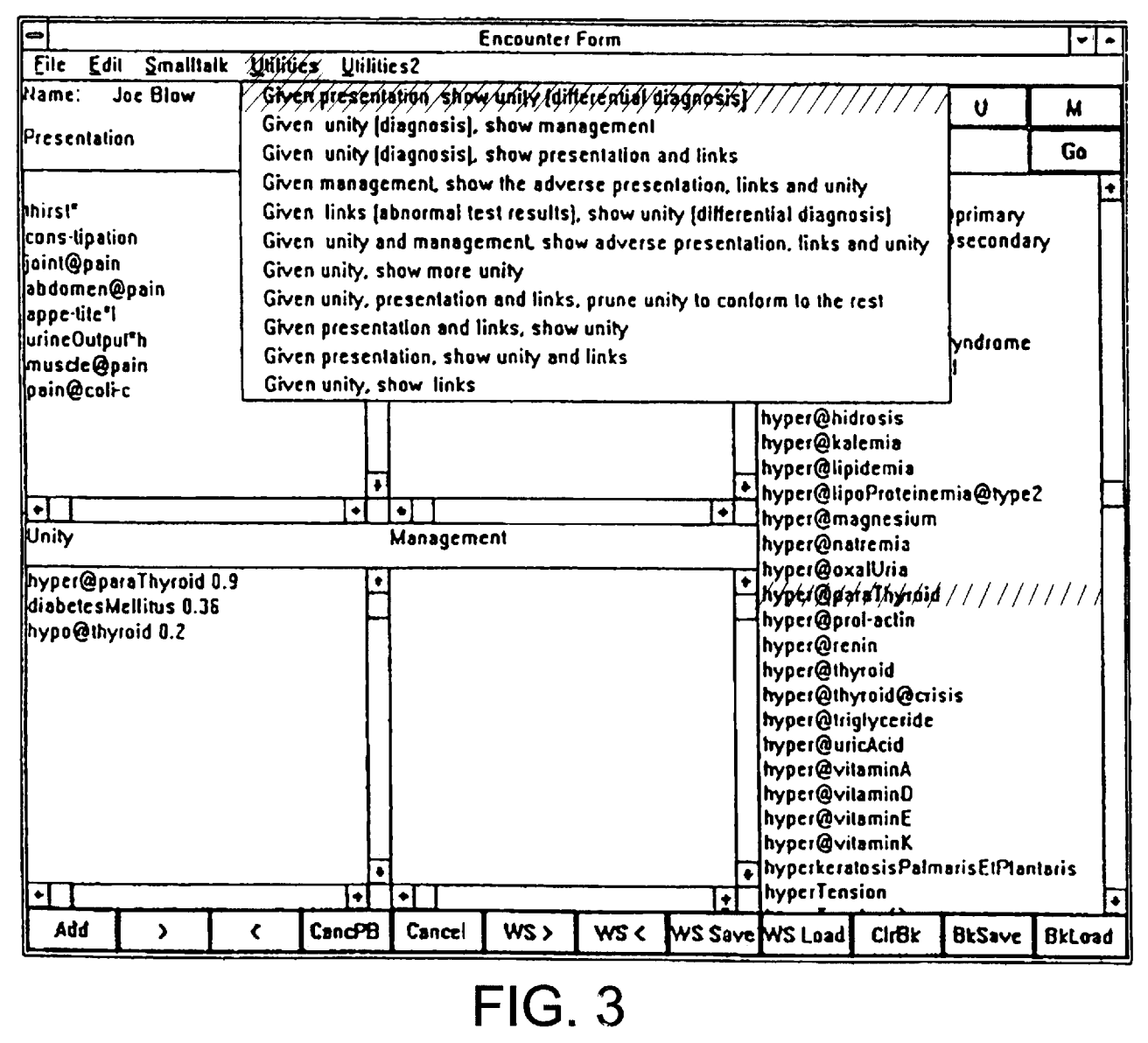

FIG. 3 shows the results of an evaluation of the type P→U.

Figure 4:
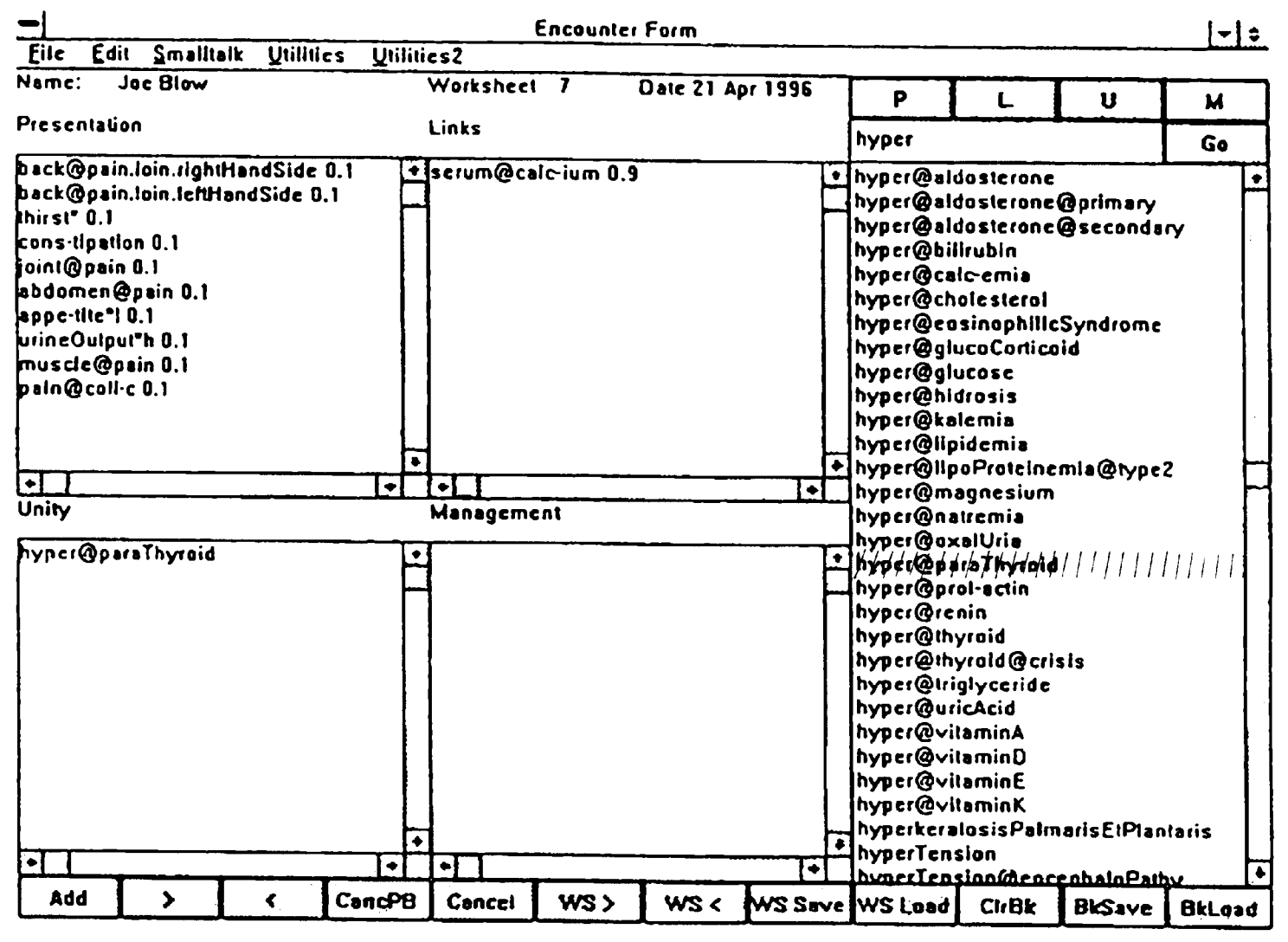

FIG. 4 shows an evaluation of the type U→PL.

Figure 5:
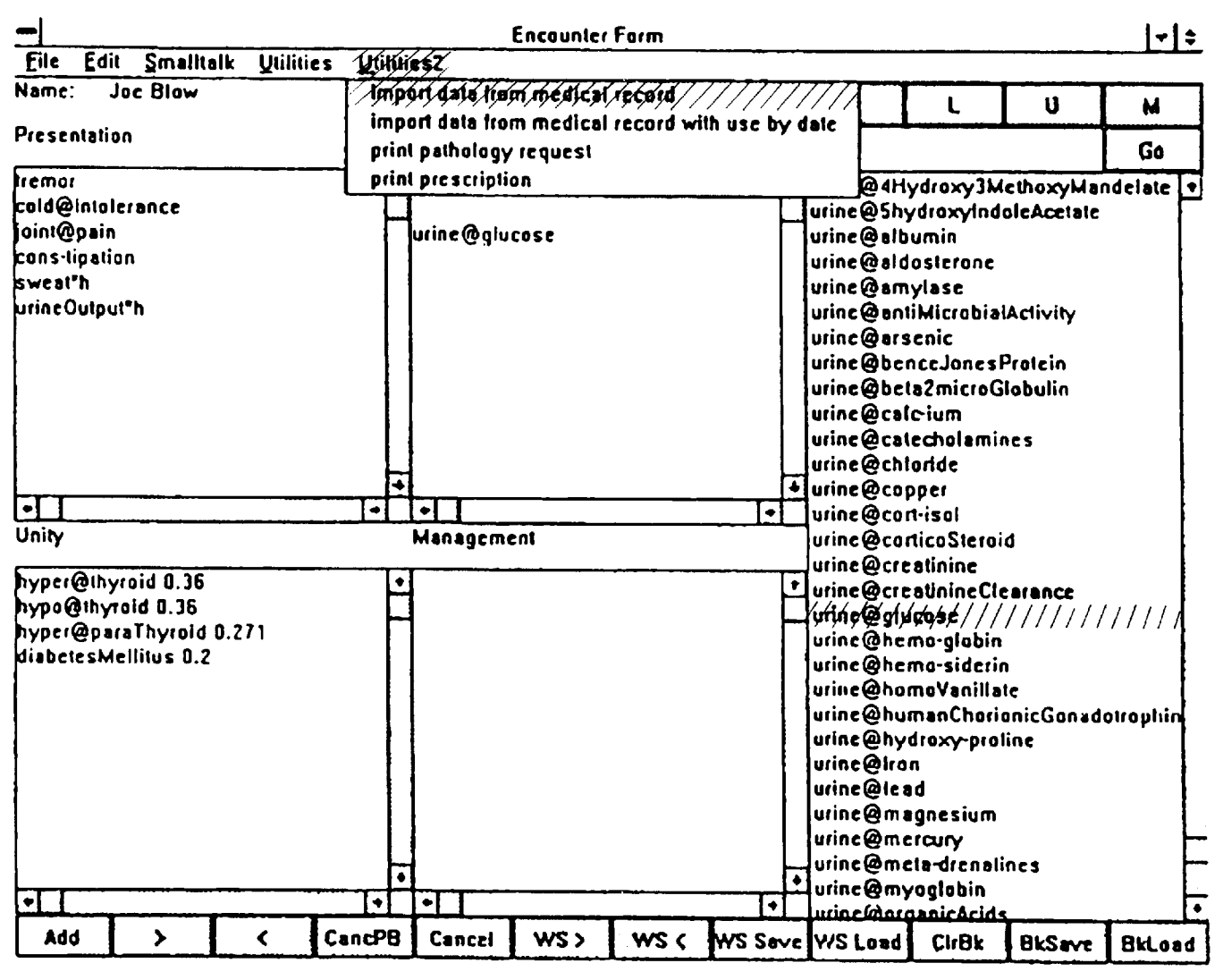

FIG. 5 shows evaluation of the type P L→U. First of a sequence of five screens.

Figure 6:
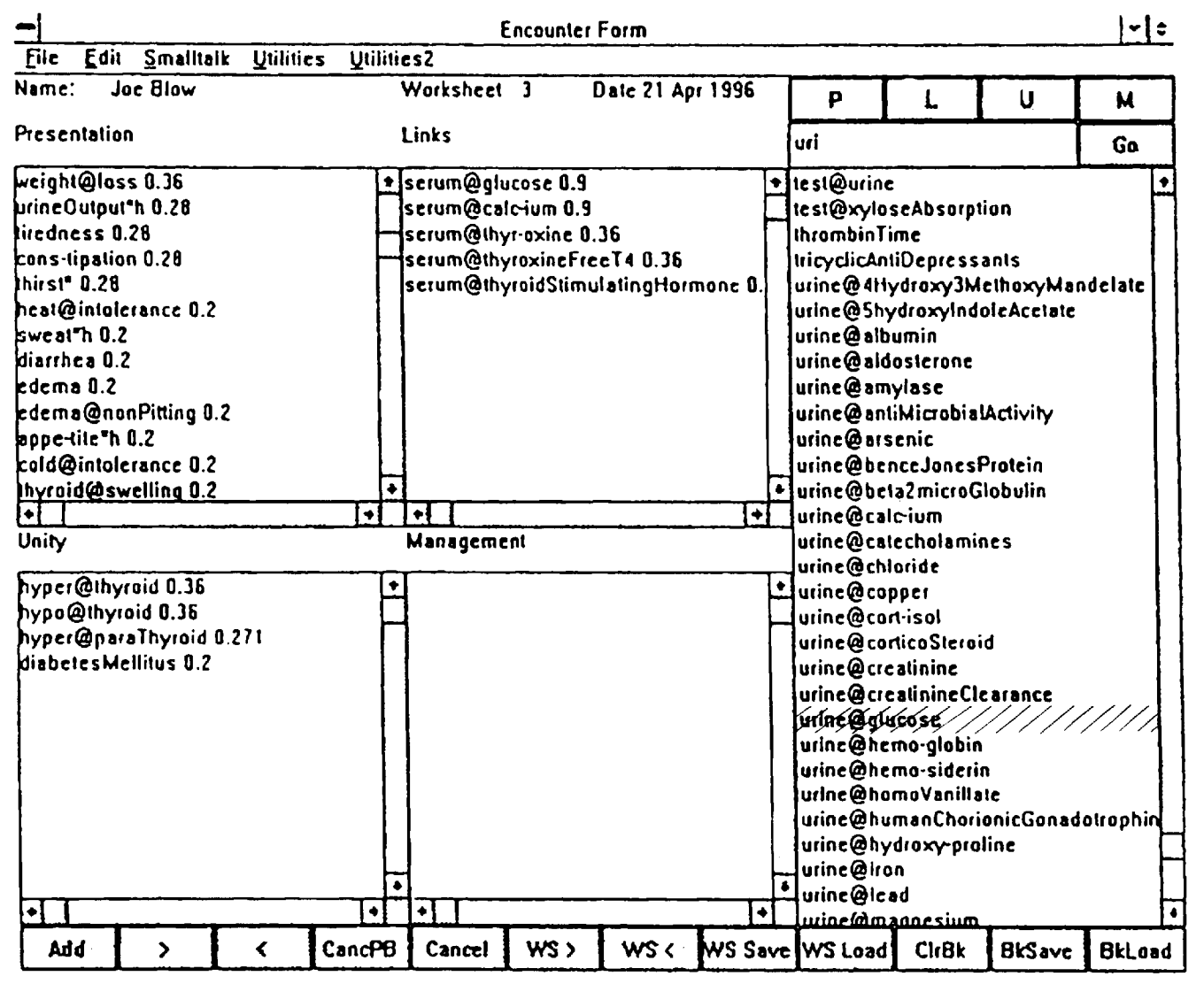

FIG. 6 shows evaluation of the type U→PL.

Figure 7:
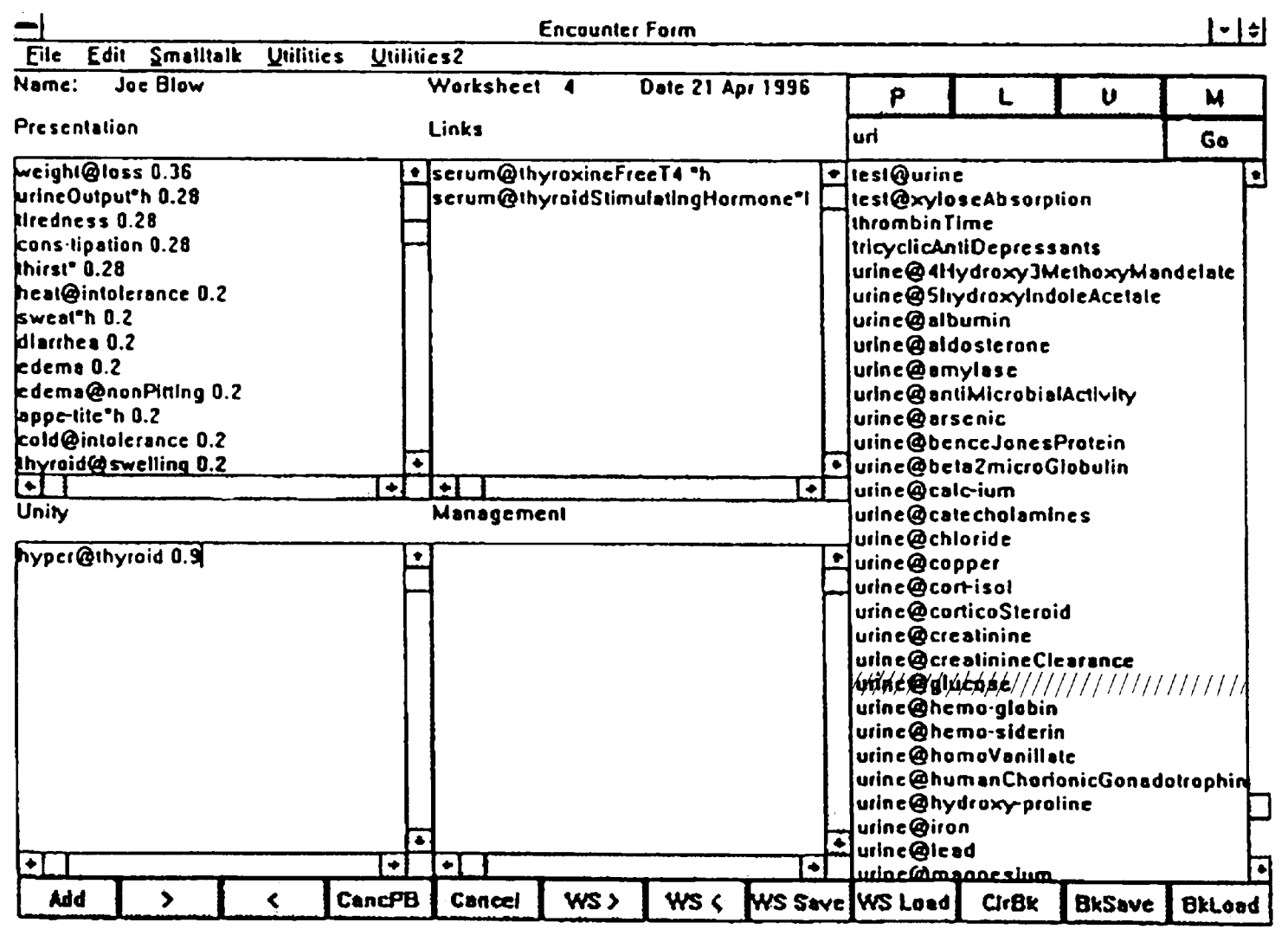

FIG. 7 shows evaluation of type L→U.

Figure 8:
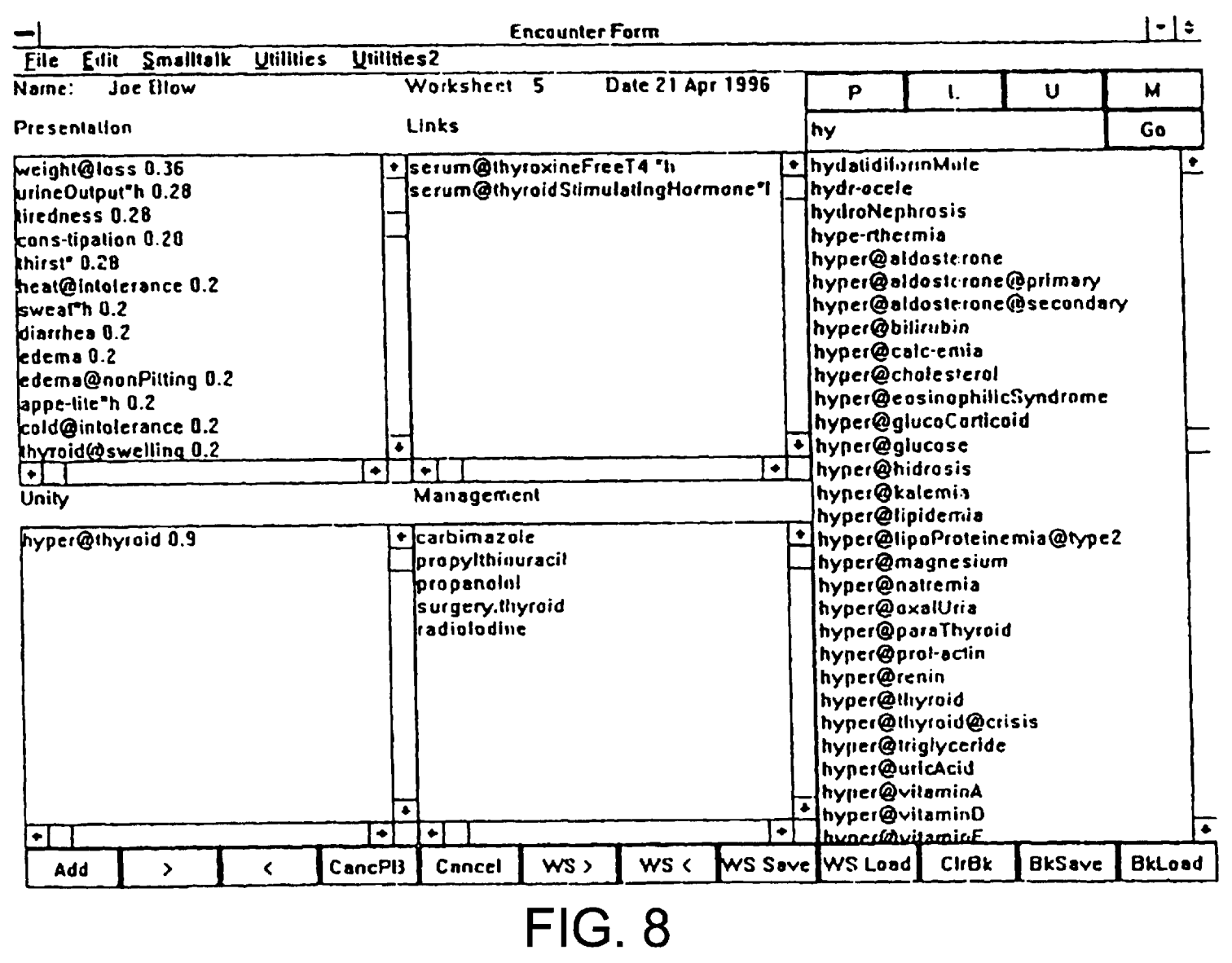

FIG. 8 shows evaluation of type U→M.

Figure 9:
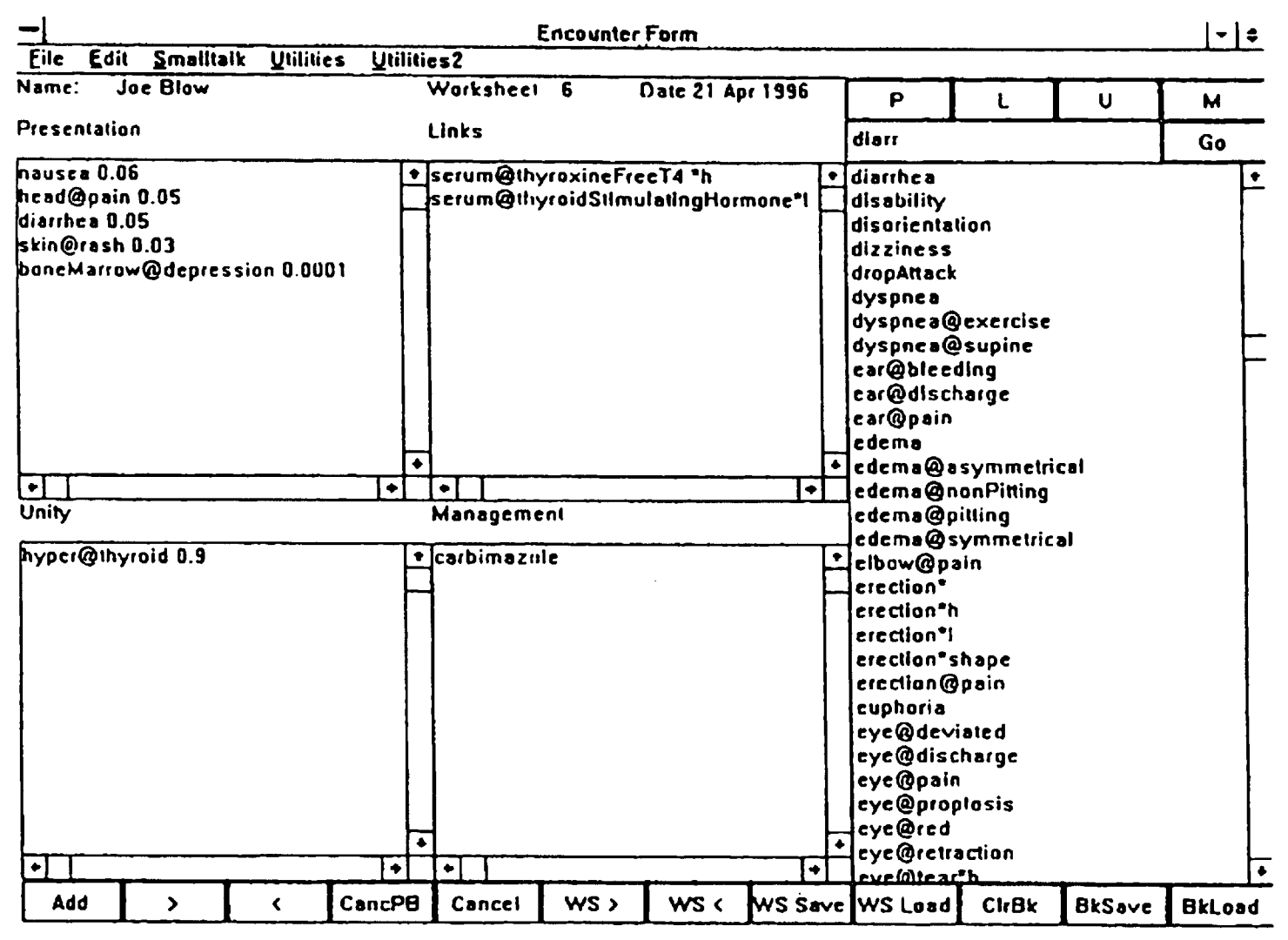

FIG. 9 shows evaluation of type M→P.

Figure 10:
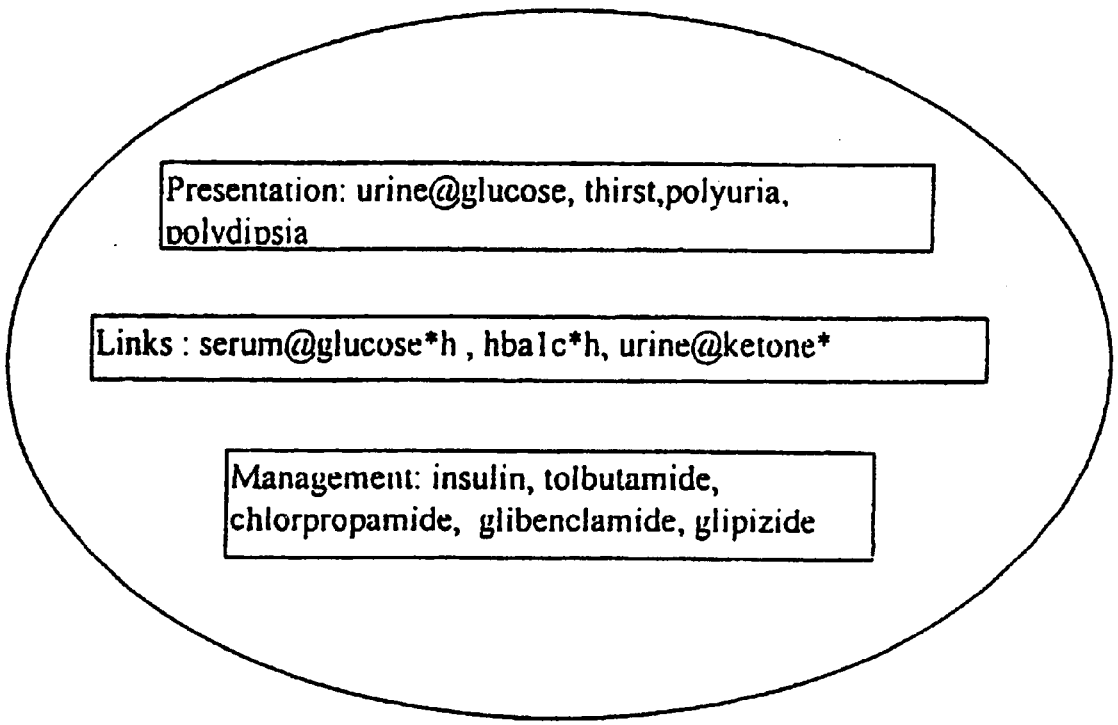

FIG. 10 shows a Unity (well defined) medical object called diabetesMellitus.

Figure 11:
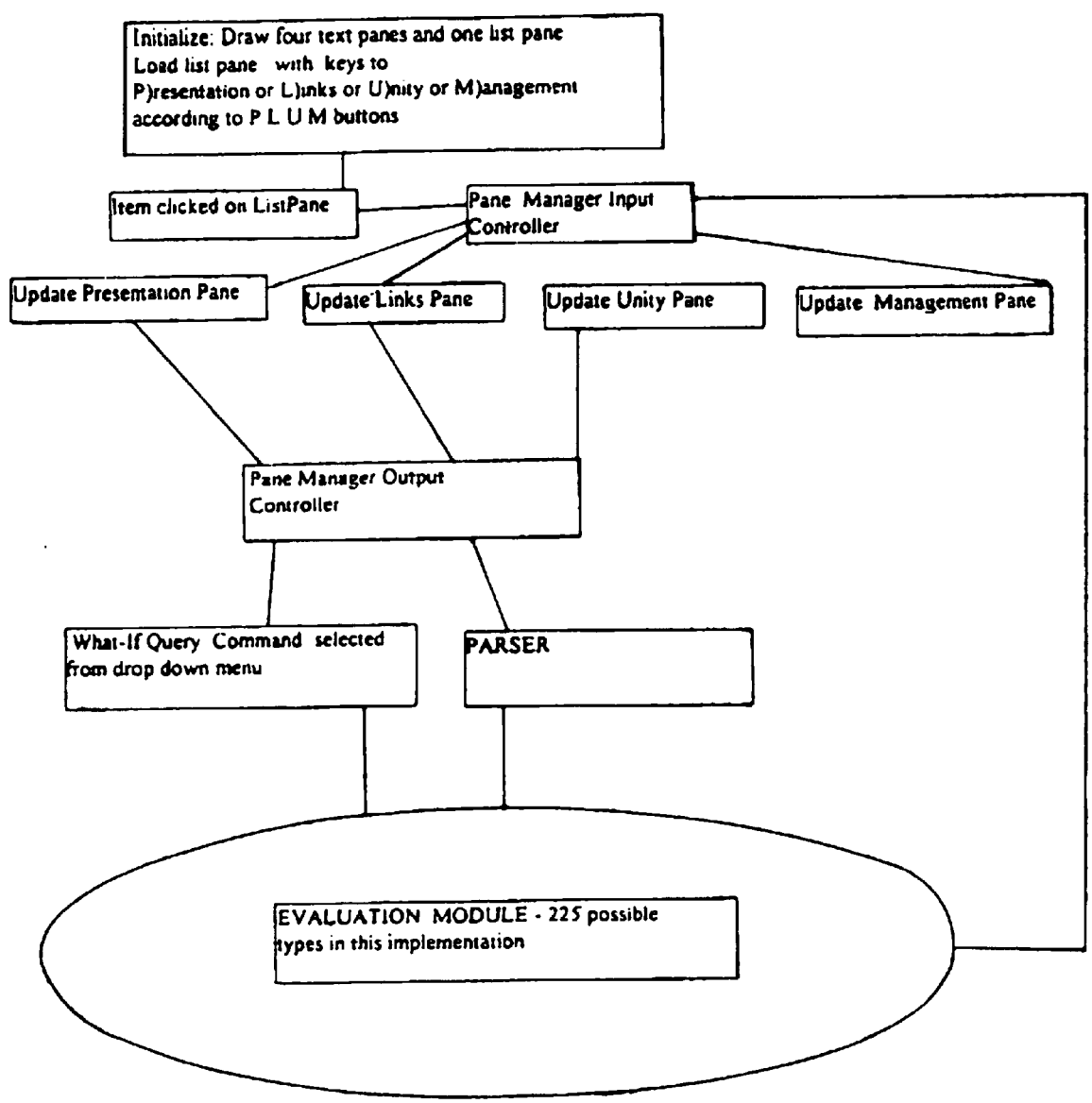

FIG. 11 shows the flow chart and components of a medical spreadsheet.

Figure 12:
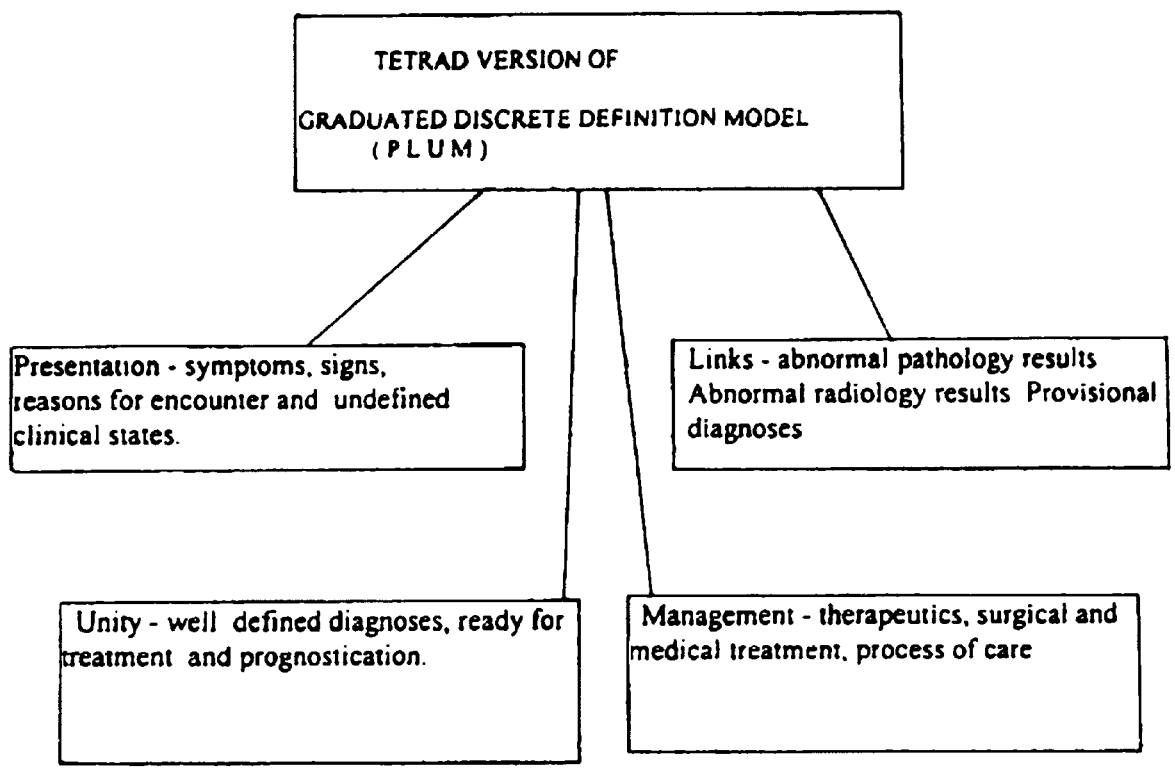

FIG. 12 shows the classification of medical objects in the tetrad version of the Graduated Discrete Definition Model.

Figure 13:
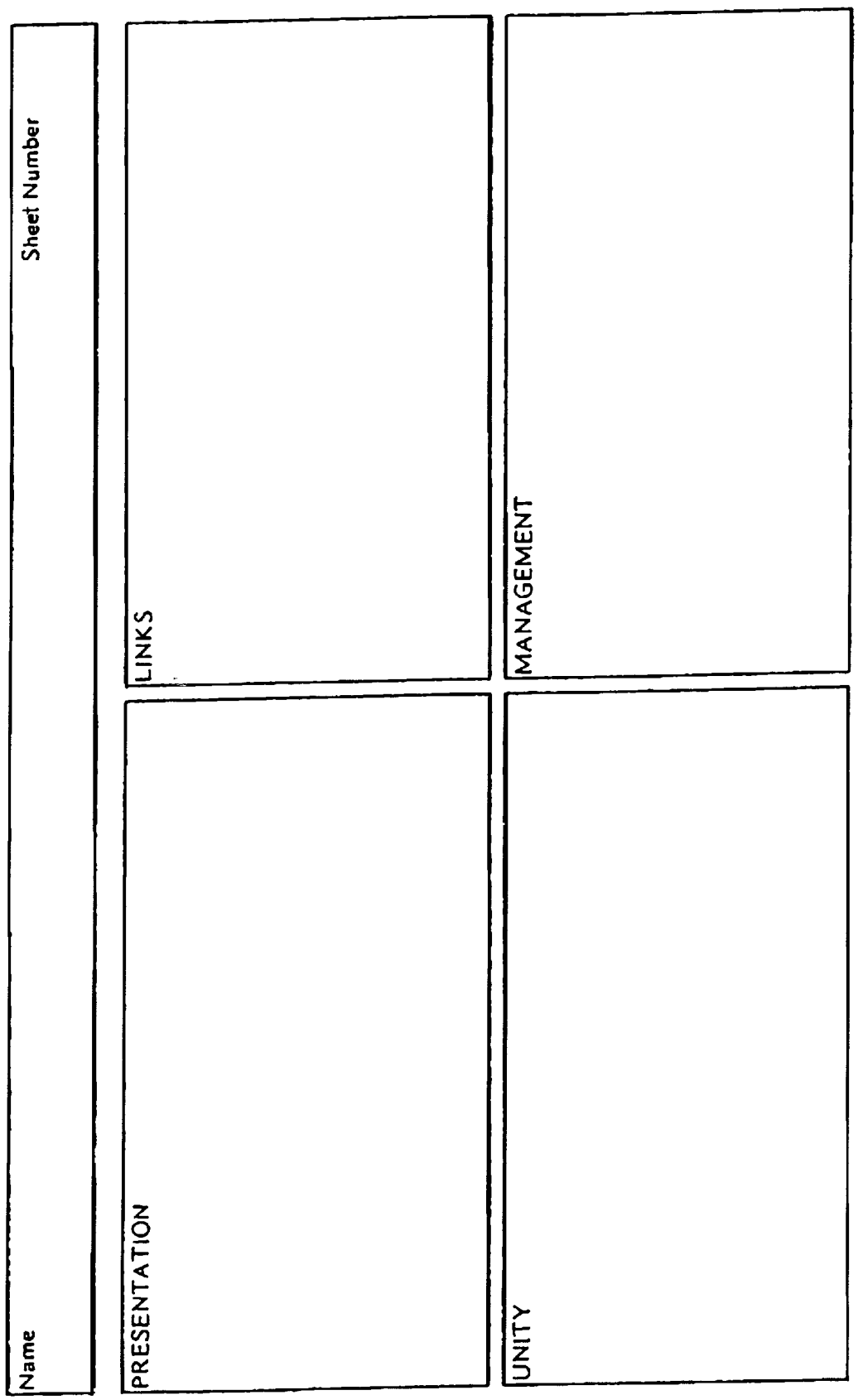
Figure 14:
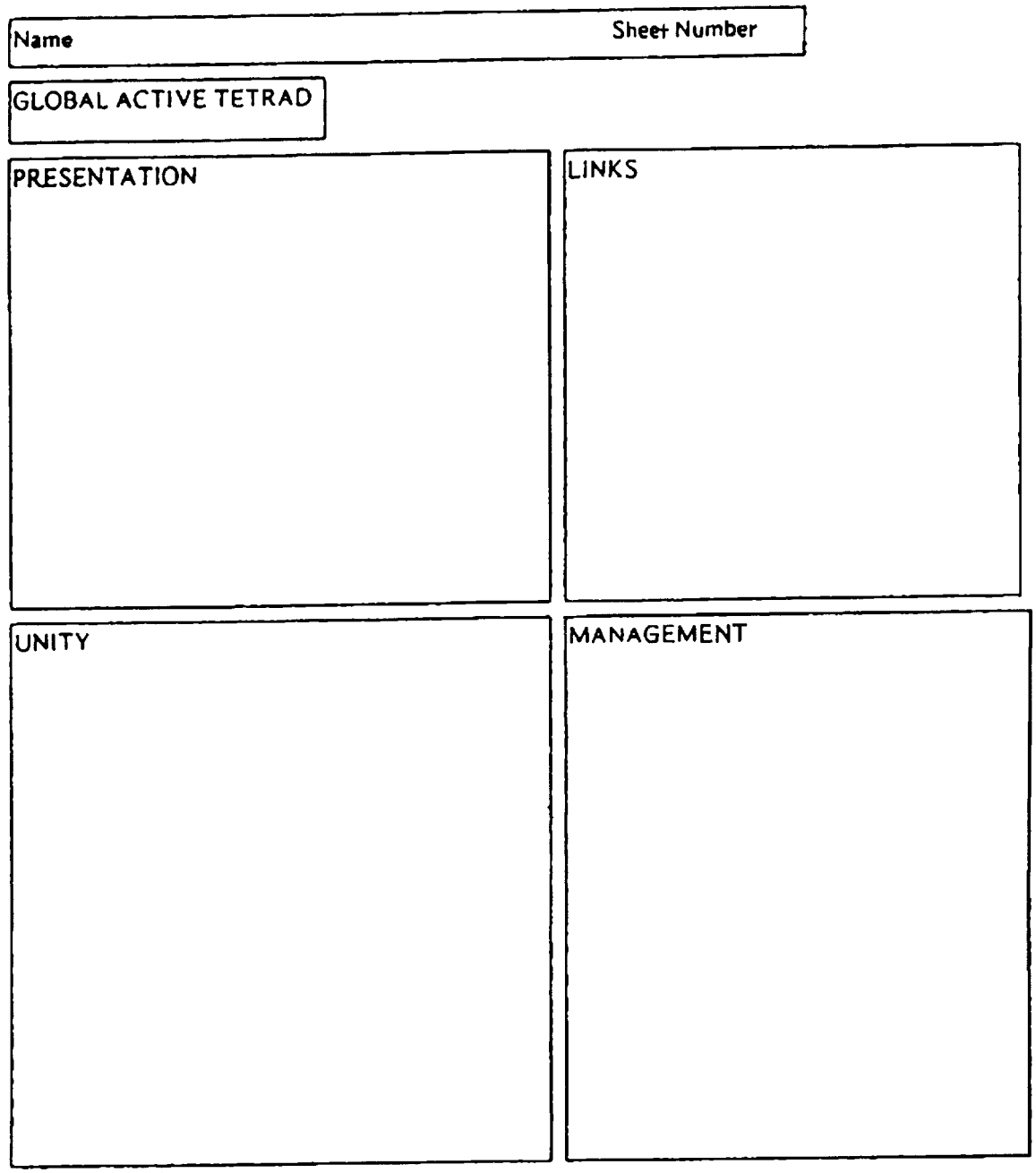
Figure 15:
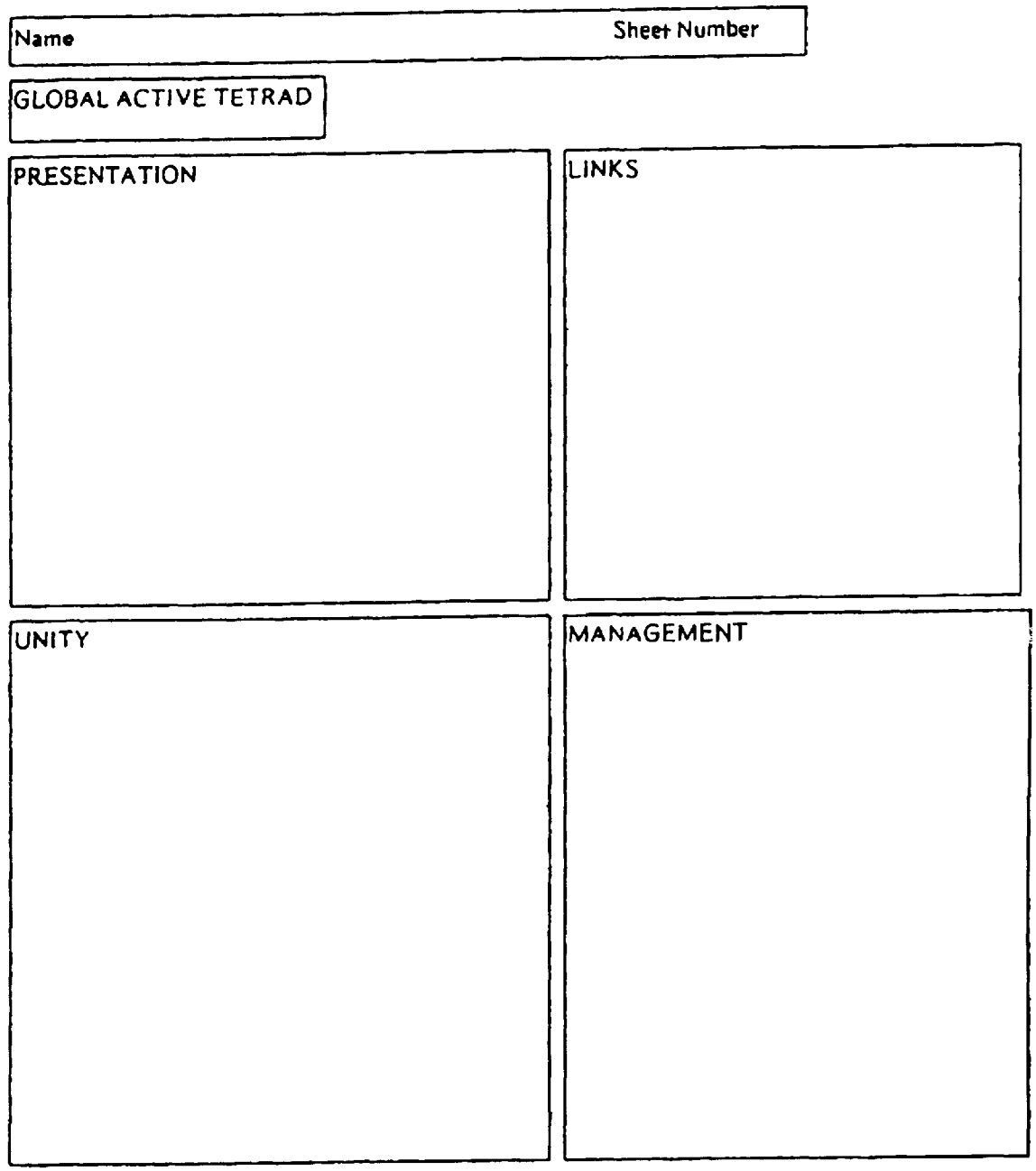
Figure 17:
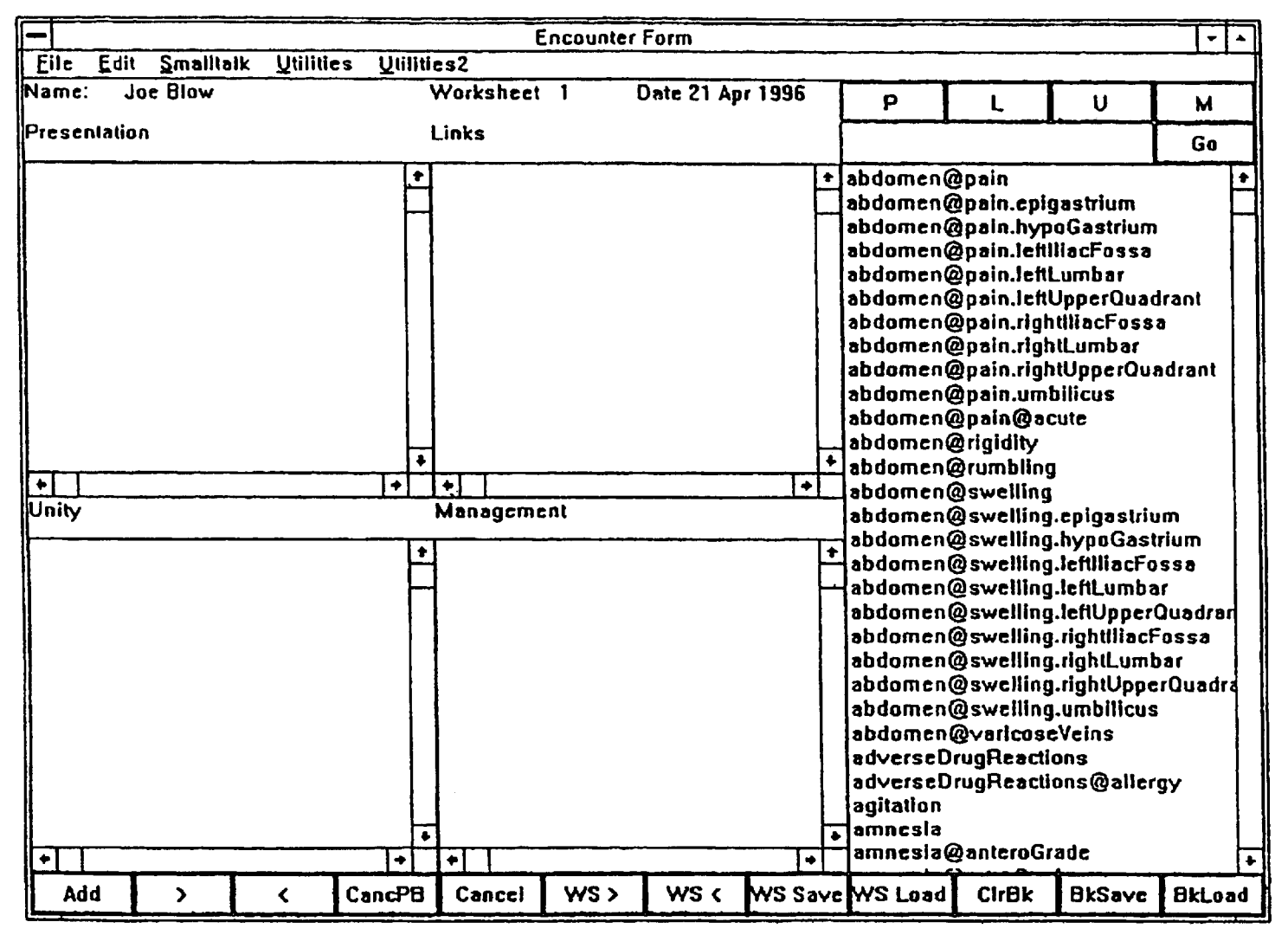
Figure 18:
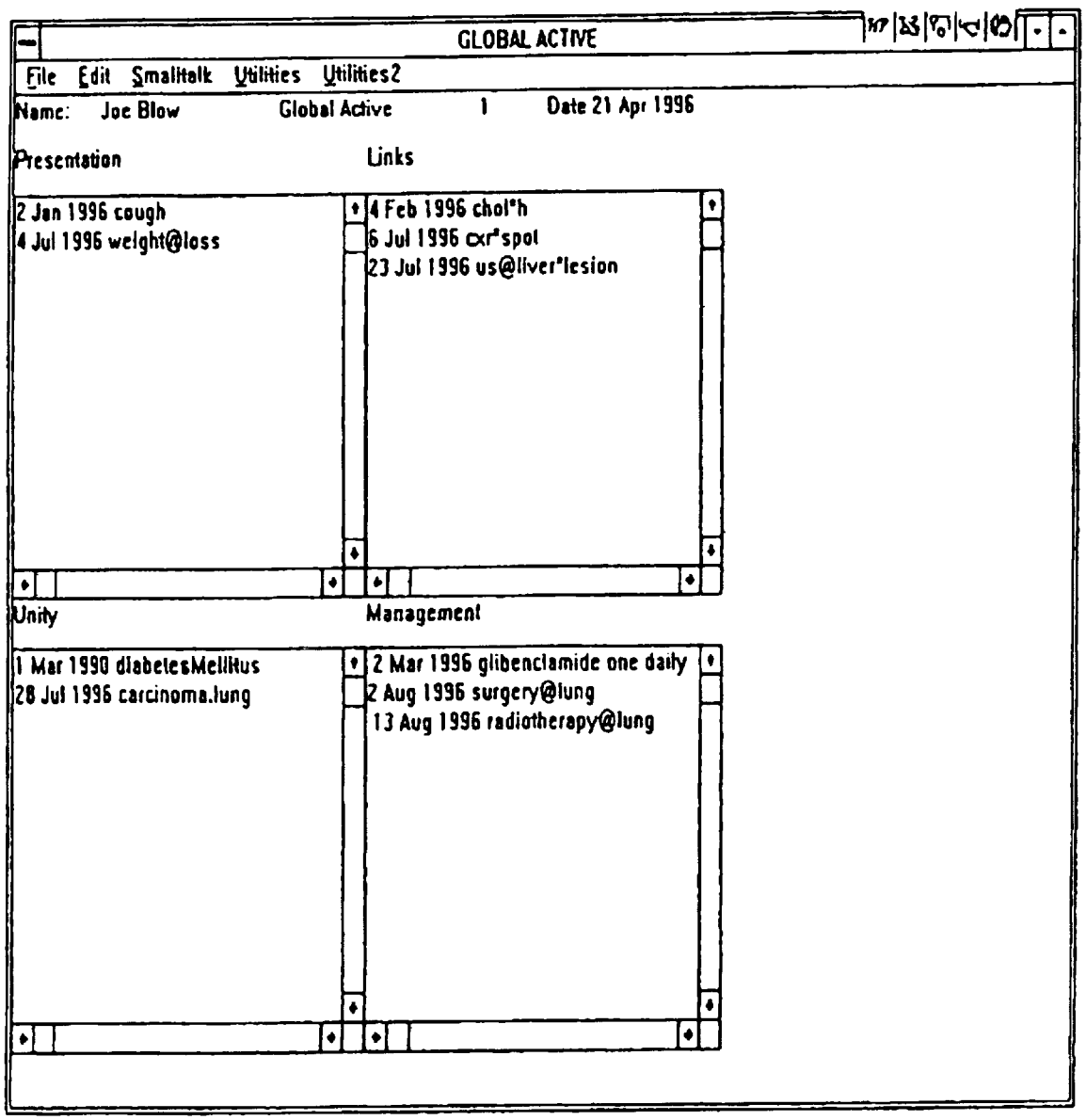
Figure 19:
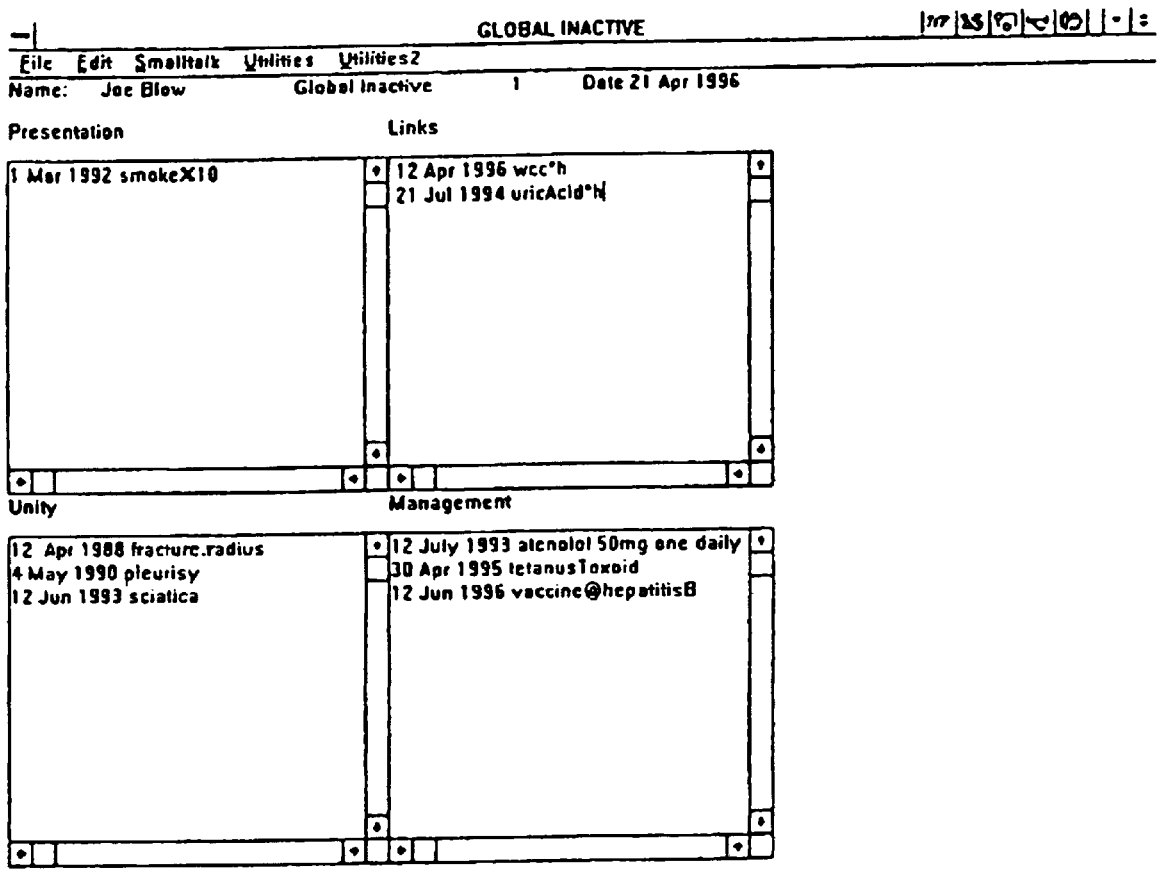
Figure 20:
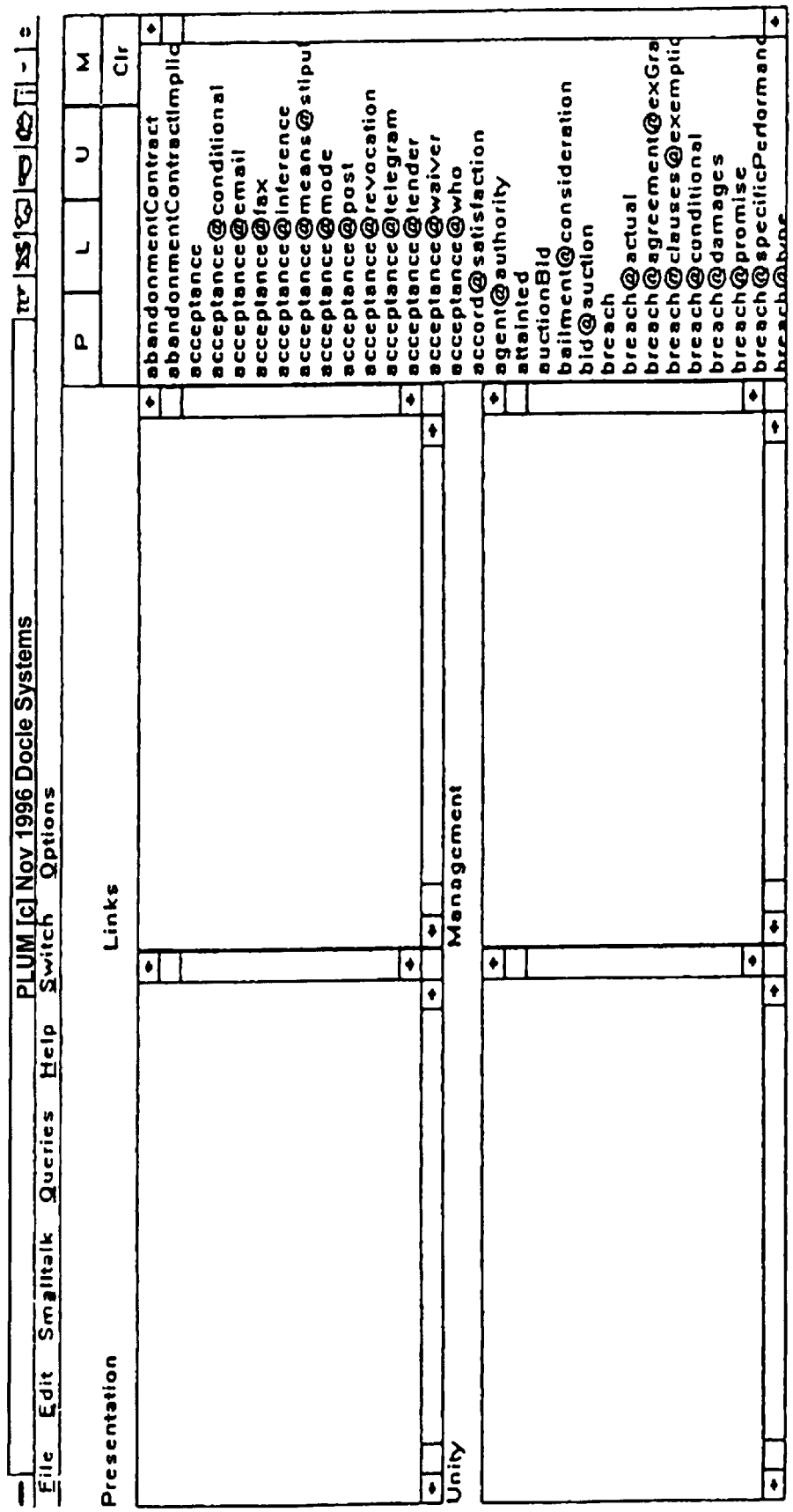

FIG. 13 shows an encounter tetrad scanning sheet for hybrid manual/electronic system FIG. 14 shows a global active tetrad sheet for manual system FIG. 15 shows a global inactive tetrad sheet for manual system FIG. 16 shows an encounter sheet for manual system FIG. 17 shows an encounter tetrad screen for electronic system FIG. 18 shows a global active tetrad screen for electronic system FIG. 19 shows global inactive tetrad screen for electronic system FIG. 20 is a legal spreadsheet based on the tetrad version of the Graduated Discrete Definition Model.

The four main cells are labelled Presentation, Links, Unity and Management. The pick list is on the right. It contains a list of presentation objects. The panes can be implemented as list boxes or text panes. The contents of the pick list can be altered by choosing any of the PL UM buttons sitting superior to the search pane. The pick list changes dynamically with input into the search pane at the top of the pick list.

Figure 21:
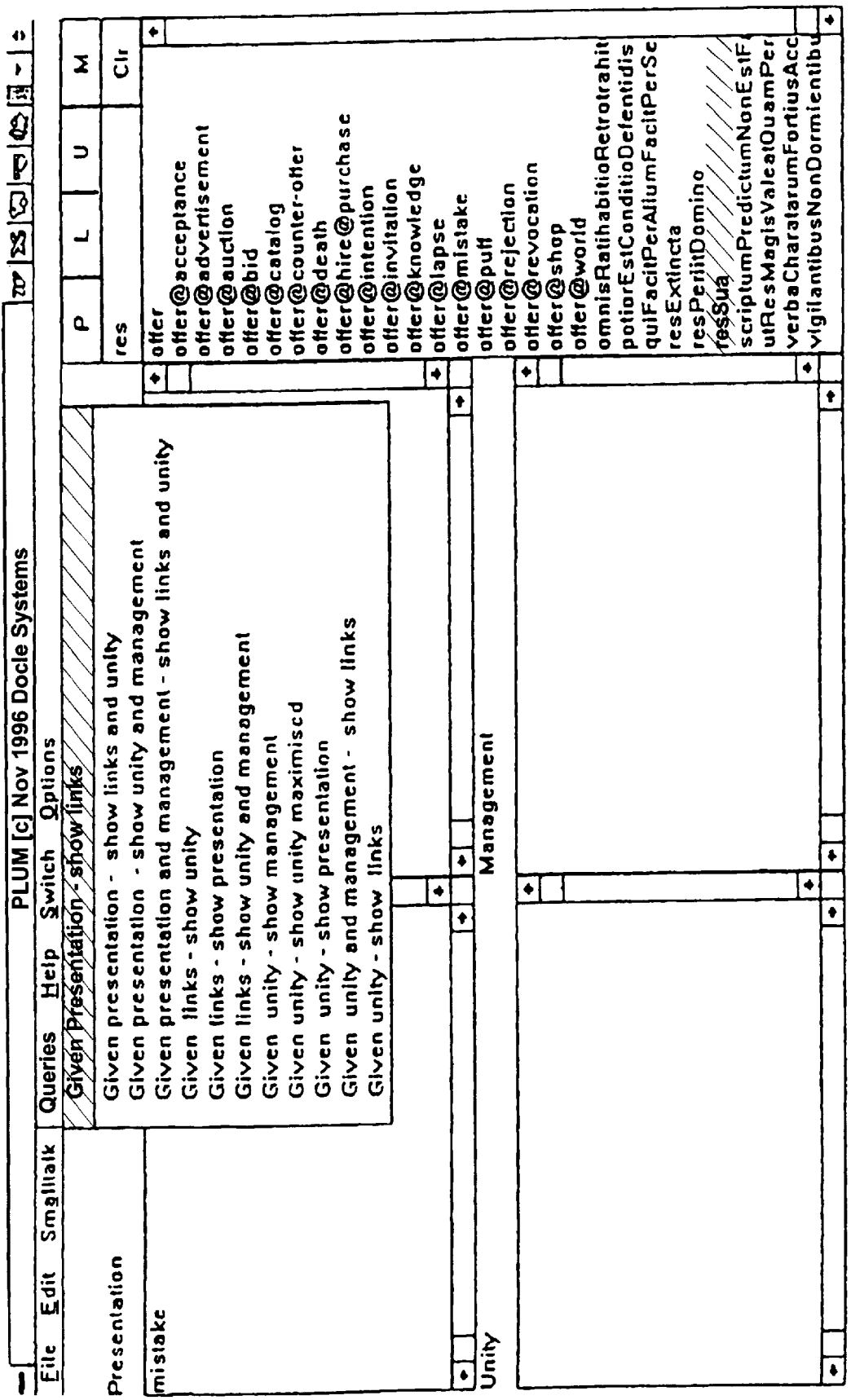

FIG. 21 shows drop down menu of the commoner types of queries of the legal spreadsheet of FIG. 20.

The client has entered into a contract tainted by mistake and wants it annulled. So the presentation item called mistake has been selected and automatically posted in the presentation pane. We are about to select the query P→UM which reads as "Given presentation, show unity and management".

Figure 22:
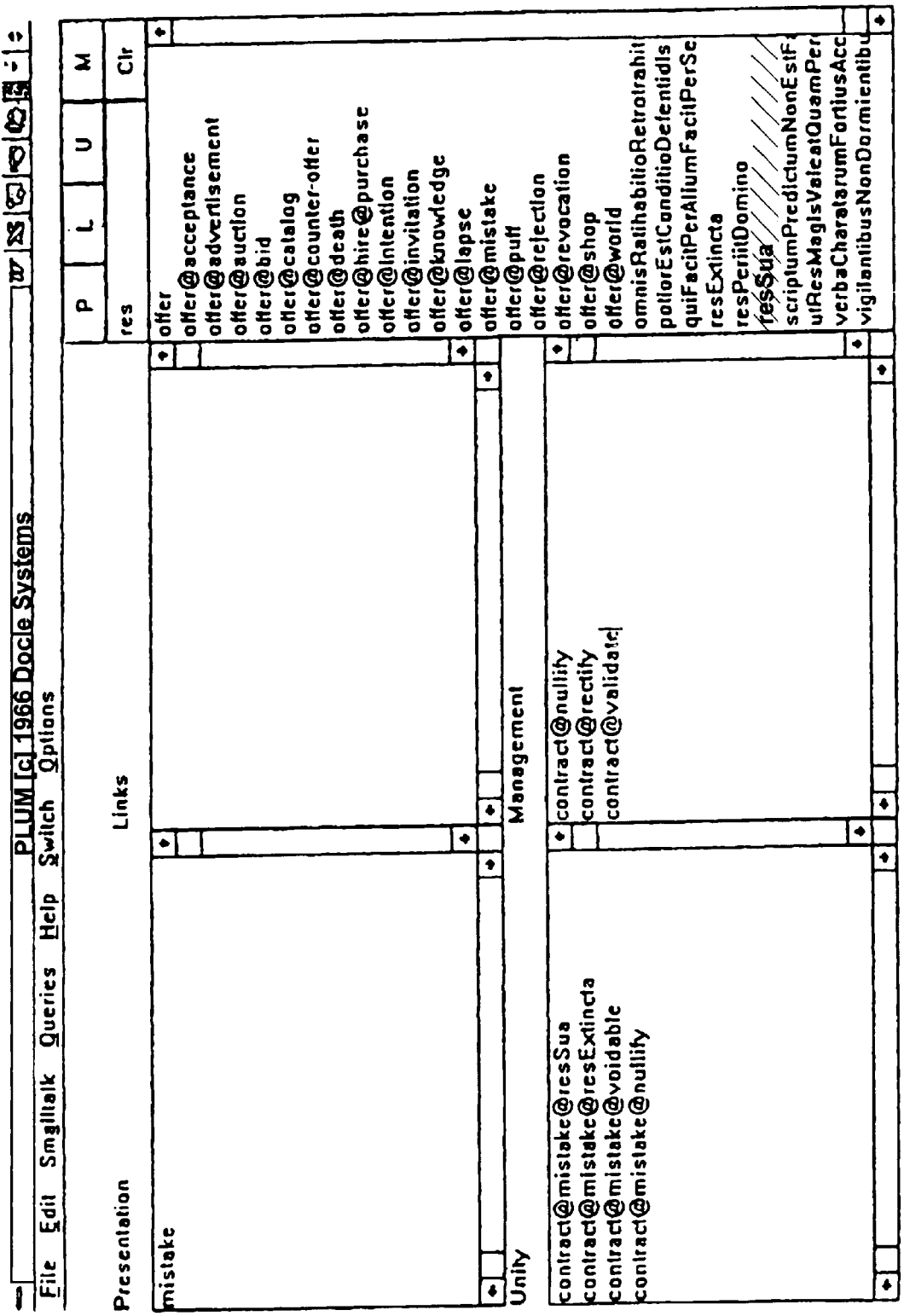

FIG. 22 shows the results of such an evaluation of the type P→UM based on the spreadsheet knowledge base of contract law.

Figure 23:
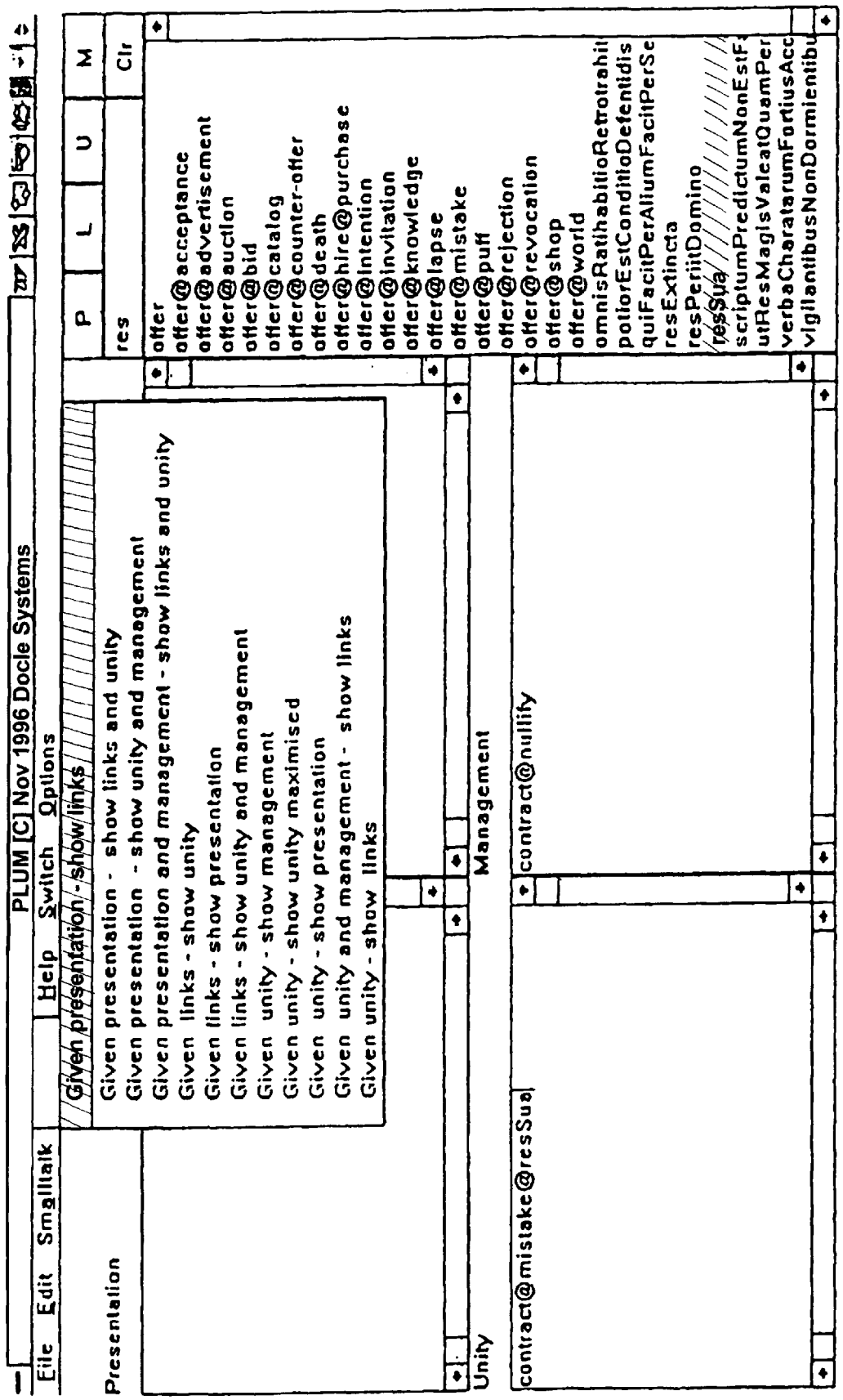

FIG. 23 shows editing of the panes by deleting all except the legal remedy of contract@nullify and the legal diagnosis of contract@mistake@resSua. The next query is UM→L which is "Given unity and management, show links".

Figure 24:
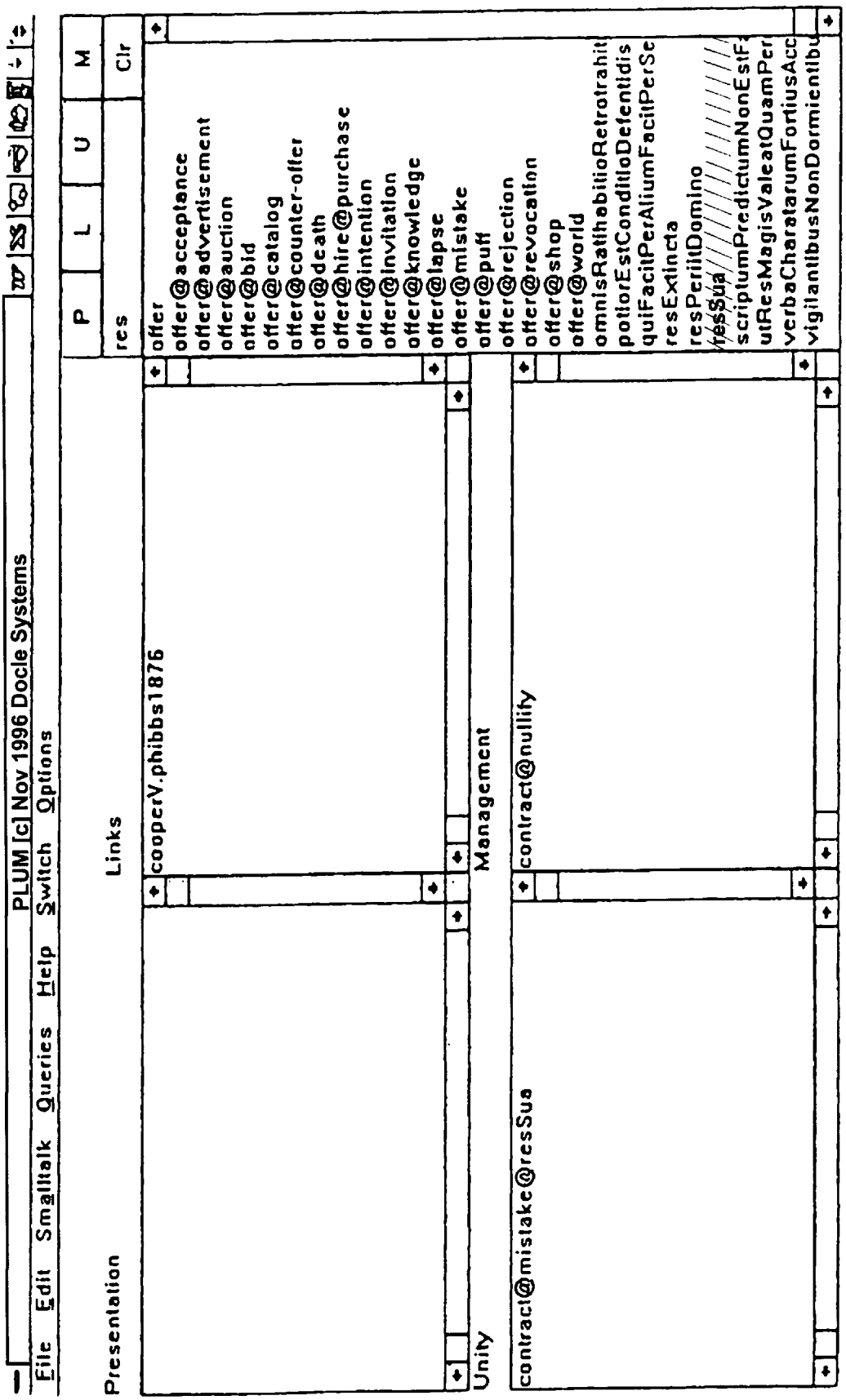

FIG. 24 shows evaluation of the type UM→L. It finds the Link or precedent cooperV.phibbs in its knowledge base. Details of the case can be obtained after selection of the legal precedent.

Figure 25:
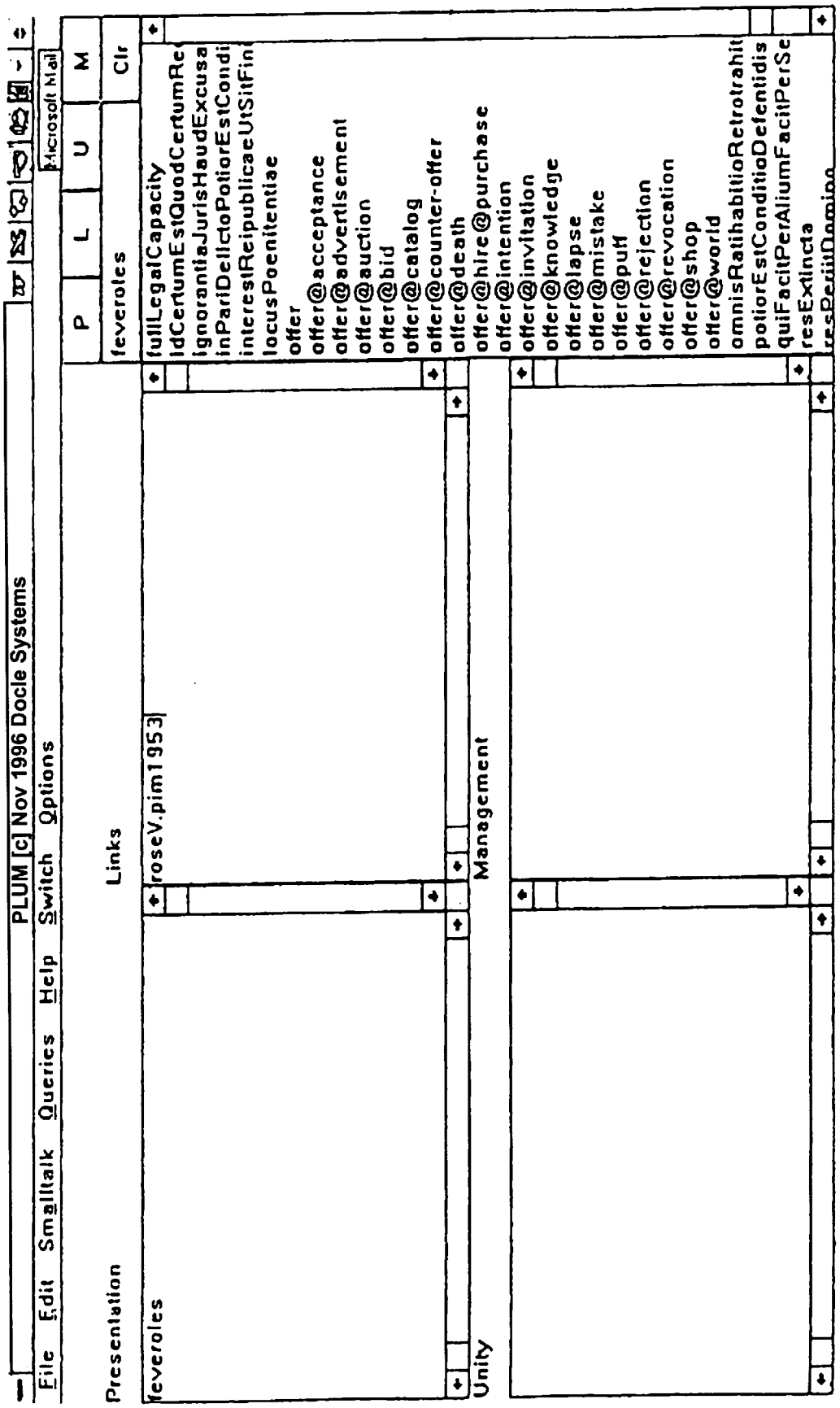

FIG. 25 shows evaluation of the type P→L. This shows that by having a presentation item called feveroles and invoking the above query will lead to the precedent of roseV.pim. The next step may be to invoke a query such as P→UM.

Figure 26:
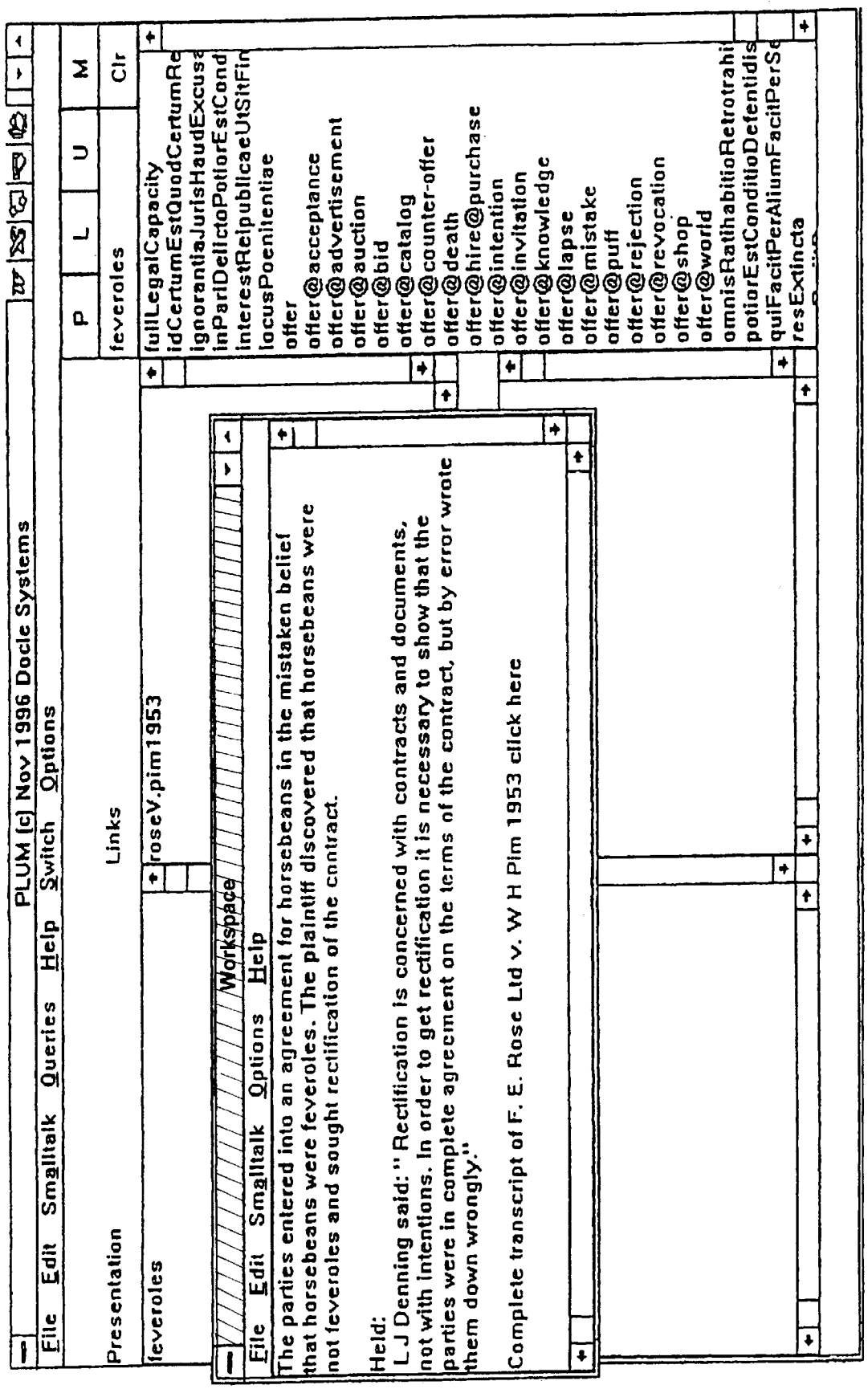

FIG. 26 shows that clicking on the precedent of roseV.pim will bring up a summary of the case, there is option to look up a more detailed transcript.

GLOSSARY

ATBD About To Be Defined, category sandwiched between Not Yet Defined and Well Defined, same as Links.

Encounter data client data built up over a single encounter.

GDDM Graduated Discrete Definition Model—knowledge representational system based on degree of definition along spectrum of being undefined to well defined, graduated because of marked intervals, discrete because the categories are mutually exclusive, definition because it is the criterion used.

Global active data cumulative client data that is still relevant today.

Global data cumulative client data build up over previous encounters.

Global inactive data cumulative client data that while not relevant today, may be relevant in the future, also data that was formerly global active.

Global log data cumulative client data, includes all encounter, global active and global inactive events.

Global status form is the generic name meaning the Global active data and/or Global inactive data.

Links about to be defined events like investigation results that do not provide a conclusive diagnosis and provisional diagnosis eg chest x ray with spot in lung, elevated white cell count in full blood examination, ?diabetes. In the legal spreadsheet equivalent, they are the legal precedents.

Management treatment and diagnostic events eg chest x ray sputum cytology—but results of such investigations are placed in Links. Treatment includes procedures and drug prescriptions. Management describes those diagnostic and treatment actions instigated by the clinician. These actions are of either the diagnostic or treatment type. In the legal spreadsheet equivalent, legal sentencing or remedies.

NYD Not Yet Defined, starting category in the GDDM, same as Presentation.

PLUM acronym for Presentation, Links, Unity and Management that form the tetrad categories of the Graduated Discrete Definition Model.

Presentation Not Yet Defined (NYD) events eg symptoms, signs and reasons for encounter—such as cough, abdominal pain and jaundice. In the legal spreadsheet equivalent, they are the attributes of a legal problem not belonging to other categories.

Tetrad means the four category version of the Graduated Discrete Definition Model, synonymous with PLUM Unity well defined events from viewpoint of treatment and prognostication eg carcinoma lung, tuberculosis. In the legal spreadsheet equivalent, the well defined legal principles or statute laws upon which judgement sits.

WD Well Defined or third category in the tetrad model, describes degree of definition suitable for treatment or prognostication, same as Unity.

It will be apparent to those skilled in the art that the method and system described above can be varied and altered without departing from the spirit of the invention. Such variations and alterations are to be understood to be included in the scope of the invention.

What is claimed is:

1. A method of implementing a computer-assisted iterative problem solving technique which starts from initial non-numerical data items and develops possible solutions within a framework of an interrelationship among preselected non-numerical data items which are divided into a plurality of mutually exclusive categories, including the steps of:

displaying on a video display, a work sheet having a plurality of cells each corresponding to one of said mutually exclusive categories for displaying the non-numerical data items;

entering initial non-numerical data items into respective cells in the work sheet;

receiving a selection of a query designating at least a first cell in the work sheet with the initial non-numerical data items as an input and requesting related non-numerical data items for at least one cell of the plurality of cells in the work sheet;

identifying non-numerical data items for the at least one cell that are related to non-numerical data items in the first cell; and inserting the identified non-numerical data items into the at least one cell in the work sheet as further information for consideration in developing possible solutions.

2. A method as in claim 1, wherein the step of entering includes displaying a pick list of non-numerical data items on the video display, selecting an entry of the pick list, and displaying the selected entry in a respective cell in the work sheet.

3. A method as in claim 1, wherein the step of entering includes receiving through an input device an alphanumeric input indicating a non-numerical data item.

4. A method as in claim 3, wherein the step of entering further includes parsing the received alphanumeric input to determine the indicated non-numerical data items.

5. A method as in claim 1, further including providing a plurality of program objects each corresponding to one of the pre-selected non-numerical data items, and wherein the step of identifying includes transmitting a request for related data items according to the query to program objects corresponding to the non-numerical data items in the first cell.

6. A method as in claim 1, further including saving contents of the cells in the work sheet before the query as one spreadsheet page.

7. A method as in claim 1, wherein the mutually exclusive categories include categories differentiated according to readiness for decision making.

8. A method as in claim 1, wherein the mutually exclusive categories consist of four categories.

9. A method as in claim 1, wherein the step of identifying includes obtaining non-numerical data items for a further cell in the work sheet that are related to the non-numerical data items in the first cell, and obtaining non-numerical data items for the at least one cell that are related to the obtained non-numerical data items for the further cell.

10. A method as in claim 1, further including displaying a probability of occurrence associated with at least one of the identified related data items in the at least one cell.

11. A method as in claim 1, wherein the pre-selected non-numerical data items include clinical data.

12. A method as in claim 1, wherein the pre-selected non-numerical data items include legal data.

13. A method of implementing a computer-assisted iterative clinical problem solving technique which starts from initial clinical data items and develops possible solutions within a framework of an interrelationship among preselected clinical data items which is divided into a plurality of mutually exclusive categories, including the steps of:

displaying on a video display a work sheet having a plurality of cells each corresponding to one of said mutually exclusive categories for displaying the clinical data items;

entering initial clinical data items into respective cells in the work sheet;

receiving a selection of a query designating at least a first cell in the work sheet with the initial clinical data items as an input and requesting related clinical data items for at least one cell of the plurality of cells in the work sheet;

identifying clinical data items for the at least one cell that are related to clinical data items in the first cell according to the query; and inserting the identified clinical data items into the at least one cell in the work sheet as further information for consideration in developing possible solutions.

14. A method as in claim 13, wherein the step of entering includes displaying a pick list of clinical data items on the video display, selecting an entry of the pick list, and displaying the selected entry in a respective cell in the work sheet.

15. A method as in claim 13, further including providing a plurality of program objects each corresponding to one of the pre-selected clinical data items, and wherein the step of identifying includes transmitting a request for related clinical data items to program objects corresponding to the clinical data items in the first cell.

16. A method as in claim 13, further including saving contents of the cells in the work sheet before the query as one spreadsheet page.

17. A method as in claim 13, wherein the mutually exclusive categories include categories differentiated according to readiness for diagnosis.

18. A method as in claim 17, wherein the mutually exclusive categories include a first category which includes symptoms and signs, a second category which includes clinical test results, and a third category which includes diagnoses.

19. A method as in claim 18, wherein the mutually exclusive categories further include a fourth category which includes prescribed treatment and investigations.

20. A method as in claim 13, wherein the step of identifying includes obtaining clinical data items for a further cell in the work sheet that are related to the clinical data items in the first cell, and obtaining clinical data items for the at least one cell that related to the obtained clinical data items for the further cell.

21. A method as in claim 13, further including displaying a probability of occurrence associated with at least one of the identified related clinical data items in the at least one cell.

22. A method of implementing a computer-assisted iterative legal problem solving technique which starts from initial legal data items and develops possible solutions within a framework of an interrelationship among preselected legal data items which is divided into a plurality of mutually exclusive categories, including the steps of:

displaying on a video display a work sheet having a plurality of cells each corresponding to one of said mutually exclusive categories for displaying the legal data items;

entering initial legal data items into respective cells in the work sheet;

receiving a selection of a query designating at least a first cell in the work sheet with the initial legal data items as an input and requesting legal data items for at least one cell of the plurality of cells in the work sheet that are related to legal data items in the first cell;

identifying legal data items for the at least one cell that are related to the legal data items in the first cell according to the query; and inserting the identified legal data items into the at least one cell in the work sheet as further information for consideration in developing possible solutions.

23. A method as in claim 22, wherein the step of entering includes displaying a pick list of legal data items on the video display, selecting an entry of the pick list, and displaying the selected entry in a respective cell in the work sheet.

24. A method as in claim 22, further including providing a plurality of program objects each corresponding to one of the pre-selected legal data items, and wherein the step of identifying includes transmitting a request for related legal data items according to the query to program objects corresponding to the legal data items in the first cell.

25. A method as in claim 24, further including assigning a key term for each of the pre-selected legal data items for identifying the program object corresponding to said each pre-selected legal data item and for representing said each pre-selected legal data item in a respective cell in the work sheet.

26. A method as in claim 22, further including saving contents of the cells of the work sheet before the query as one spreadsheet page.

27. A method as in claim 22, wherein the mutually exclusive categories include categories differentiated according to readiness for adjudication.

28. A method as in claim 27, wherein the mutually exclusive categories include a first category which includes dispute-related facts, a second category which includes legal precedents, and a third category which includes legal principles.

29. A method as in claim 28, wherein the mutually exclusive categories further include a fourth category which includes legal remedies.

30. A method as in claim 22, wherein the step of identifying includes obtaining legal data items for a further cell in the work sheet that are related to the legal data items in the first cell, and obtaining legal data items for the at least one cell that are related to the obtained legal data items for the further cell.

31. A method of recording patient specific clinical data for evaluation of patient status, where clinical data has been divided into a plurality of mutually exclusive categories including the steps of:

providing an encounter form which has a plurality of cells each corresponding to one of said mutually exclusive categories; and entering the patient specific clinical data collected during at least one patient encounter into respective cells in the encounter form according to the respective categories to which the collected clinical data belong.

32. A method as in claim 31, further including the steps of:

providing a global status form which has a plurality of cells each corresponding to one of said mutually exclusive categories; and posting the collected clinical data in the at least one encounter form into respective cells in the global status form.

33. A method as in claim 32, wherein the step of posting includes electronically scanning the cells of the encounter form to identify the collected clinical data and the respective categories of the collected clinical data, and storing the collected clinical data into respective cells of the global status form.

34. A method as in claim 32, further including the steps of providing a global inactive status form which has cells corresponding respectively to the mutually exclusive categories, and transferring clinical data posted in the global status form that have become inactive into respective cells in the global inactive status form.

35. A method as in claim 32, wherein the step of entering includes recording in the encounter form a date of generation for each datum of the collected clinical data.

36. A method as in claim 32, wherein the mutually exclusive categories consist of four categories.

37. A method as in claim 32, wherein the mutually exclusive categories include categories differentiated according to readiness for diagnosis.

38. A method as in claim 37, wherein the mutually exclusive categories include a first category which includes signs and symptoms, a second category which includes clinical test results, and a third category which includes diagnoses.

39. A method as in claim 38, wherein the mutually exclusive categories further include a fourth category which includes treatment and investigations.

40. A recording system for recording clinical data for evaluation of patient status including:

a reference listing having a plurality of mutually exclusive categories;

an encounter form having a plurality of cells each corresponding to to one of said mutually exclusive categories to receive;

wherein clinical data collected during at least one patient encounter is entered into respective cells in the encounter form according to the respective categories to which the collected clinical data belong.

* * * * *